United States Patent
Sumi

(10) Patent No.: US 9,993,228 B2
(45) Date of Patent: *Jun. 12, 2018

(54) DISPLACEMENT MEASUREMENT METHOD AND APPARATUS, AND ULTRASONIC DIAGNOSTIC APPARATUS

(71) Applicant: Chikayoshi Sumi, Tokorozawa (JP)

(72) Inventor: Chikayoshi Sumi, Tokorozawa (JP)

( * ) Notice: Subject to any disclaimer, the term of this patent is extended or adjusted under 35 U.S.C. 154(b) by 592 days.

This patent is subject to a terminal disclaimer.

(21) Appl. No.: 14/591,777

(22) Filed: Jan. 7, 2015

(65) Prior Publication Data
US 2015/0112185 A1    Apr. 23, 2015

Related U.S. Application Data

(62) Division of application No. 12/833,072, filed on Jul. 9, 2010, now Pat. No. 8,956,297.

(30) Foreign Application Priority Data

Sep. 10, 2009  (JP) .................................. 2009-209656
Jun. 25, 2010  (JP) .................................. 2010-144921

(51) Int. Cl.
*A61B 8/08*    (2006.01)
*G01S 7/52*    (2006.01)
(Continued)

(52) U.S. Cl.
CPC .......... *A61B 8/5223* (2013.01); *A61B 5/0059* (2013.01); *A61B 5/055* (2013.01);
(Continued)

(58) Field of Classification Search
CPC ....... A61B 8/5223; A61B 8/4466; A61B 8/54; A61B 5/055; A61B 8/463; A61B 8/42;
(Continued)

(56) References Cited

U.S. PATENT DOCUMENTS 5,148,810 A    9/1992   Maslak et al.
5,495,771 A    3/1996   Sumi et al.
(Continued)

FOREIGN PATENT DOCUMENTS

JP    60242365 A    12/1985
JP    02237554 A    9/1990
(Continued)

OTHER PUBLICATIONS

Japanese Office Action (and English translation thereof) dated Jan. 5, 2016, issued in counterpart Japanese Application No. 2014-243937.
(Continued)

*Primary Examiner* — Long V Le
*Assistant Examiner* — Angela M Hoffa
(74) *Attorney, Agent, or Firm* — Holtz, Holtz & Volek PC

(57) ABSTRACT

An accurate real-time measurement of a displacement vector is achieved on the basis of the proper beamforming that require a short time for obtaining one echo data frame without suffering affections by a tissue motion. The displacement measurement method includes the steps of: (a) yielding ultrasound echo data frames by scanning an object laterally or elevationally using an ultrasound beam steered electrically and/or mechanically with a single steering angle over an arbitrary three-dimensional orthogonal coordinate system involving existence of three axes of a depth direction, a lateral direction, and an elevational direction; and (b) calculating a displacement vector distribution by implementing a block matching on the predetermined ultrasound echo data frames yielded at more than two phases.

20 Claims, 8 Drawing Sheets

(51) Int. Cl.

| | | |
|---|---|---|
| *A61B 8/06* | (2006.01) | |
| *A61B 5/055* | (2006.01) | |
| *A61B 8/14* | (2006.01) | |
| *A61B 8/00* | (2006.01) | |
| *G01R 33/48* | (2006.01) | |
| *G06T 7/00* | (2017.01) | |
| *G01S 15/89* | (2006.01) | |
| *A61B 5/00* | (2006.01) | |
| *A61B 5/01* | (2006.01) | |
| *G01S 15/42* | (2006.01) | |

(52) U.S. Cl.
CPC ............... *A61B 8/06* (2013.01); *A61B 8/08* (2013.01); *A61B 8/145* (2013.01); *A61B 8/42* (2013.01); *A61B 8/4416* (2013.01); *A61B 8/4466* (2013.01); *A61B 8/463* (2013.01); *A61B 8/485* (2013.01); *A61B 8/54* (2013.01); *G01R 33/4814* (2013.01); *G01S 7/52042* (2013.01); *G06T 7/0016* (2013.01); *A61B 5/0048* (2013.01); *A61B 5/015* (2013.01); *A61B 8/488* (2013.01); *G01S 15/42* (2013.01); *G01S 15/899* (2013.01); *G01S 15/8977* (2013.01); *G01S 15/8979* (2013.01); *G01S 15/8997* (2013.01)

(58) Field of Classification Search
CPC ..... A61B 8/4416; A61B 5/0059; A61B 8/145; A61B 8/08; A61B 8/06; A61B 8/485; G01R 33/4814; G06T 7/0016; G01S 7/52042
See application file for complete search history.

(56) References Cited

U.S. PATENT DOCUMENTS

| | | | |
|---|---|---|---|
| 6,270,459 | B1 | 8/2001 | Konofagou et al. |
| 7,050,610 | B2 | 5/2006 | Chen et al. |
| 7,223,241 | B2 | 5/2007 | Radulescu |
| 7,690,838 | B2 | 4/2010 | Sumi |
| 7,766,836 | B2 | 8/2010 | Waki |
| 7,775,980 | B2 | 8/2010 | Sumi |
| 7,868,824 | B2 | 1/2011 | Sumi |
| 7,914,456 | B2 | 3/2011 | Osaka et al. |
| 7,946,180 | B2 | 5/2011 | Sumi |
| 7,957,609 | B2 | 6/2011 | Lu et al. |
| 8,007,438 | B2 | 8/2011 | Osaka et al. |
| 8,206,298 | B2 | 6/2012 | Matsumura et al. |
| 8,211,019 | B2 | 7/2012 | Sumi |
| 8,353,831 | B2 | 1/2013 | Matsumura |
| 8,429,982 | B2 | 4/2013 | Sumi |
| 8,696,573 | B2 * | 4/2014 | Shiina ............... A61B 8/08 600/437 |
| 8,956,297 | B2 * | 2/2015 | Sumi ............... A61B 8/06 600/438 |
| 9,084,559 | B2 * | 7/2015 | Sumi ............... A61B 8/08 |
| 2004/0034304 | A1 | 2/2004 | Sumi |
| 2005/0283076 | A1 | 12/2005 | Hangiandreou et al. |
| 2007/0093716 | A1 | 4/2007 | Radulescu |
| 2007/0167772 | A1 | 7/2007 | Radulescu |
| 2007/0232916 | A1 | 10/2007 | Waki |
| 2008/0144902 | A1 | 6/2008 | Radulescu |
| 2009/0143676 | A1 | 6/2009 | Matsumura |
| 2009/0149750 | A1 | 6/2009 | Matsumura |
| 2009/0149752 | A1 | 6/2009 | Osaka et al. |
| 2009/0177084 | A1 | 7/2009 | Matsumura et al. |
| 2010/0106018 | A1 | 4/2010 | Jiang et al. |
| 2010/0185093 | A1 | 7/2010 | Hamilton |
| 2010/0256494 | A1 | 10/2010 | Azuma |
| 2010/0268084 | A1 | 10/2010 | Osaka et al. |
| 2011/0004100 | A1 | 1/2011 | Iimura |
| 2011/0040187 | A1 | 2/2011 | Matsumura |
| 2011/0060222 | A1 | 3/2011 | Thittai et al. |
| 2011/0098563 | A1 | 4/2011 | Osaka |
| 2011/0137165 | A1 | 6/2011 | Dufour et al. |
| 2011/0137175 | A1 | 6/2011 | Hossack et al. |
| 2011/0152687 | A1 | 6/2011 | Iimura et al. |
| 2011/0160590 | A1 | 6/2011 | Waki et al. |
| 2011/0204893 | A1 | 8/2011 | Sumi |
| 2012/0278005 | A1 | 11/2012 | Sumi |
| 2013/0046175 | A1 | 2/2013 | Sumi |
| 2017/0311930 | A1 * | 11/2017 | Sumi ............... G01S 7/52042 |

FOREIGN PATENT DOCUMENTS

| | | |
|---|---|---|
| JP | 04279148 A | 10/1992 |
| JP | 06022965 A | 2/1994 |
| JP | 2006325704 A | 12/2006 |
| JP | 2007152074 A | 6/2007 |
| JP | 2007282932 A | 11/2007 |
| JP | 4260523 B2 | 4/2009 |
| WO | 2006073088 A1 | 7/2006 |

OTHER PUBLICATIONS

A Demonstration of Optical Apodization Determination for Proper Lateral Modulation; Chikayoshi Sumi et al; Japanese Journal of Applied Physics 48 (2009); 07GJ06; pp. 1-10.
A Heterodyning Demodulation Technique for Spatial Quadrature; M. E. Anderson; 2000 IEEE Ultrasonics Symposium.
A New Estimator for Vector Velocity Estimation; Jorgen Arendt Jensen; IEEE Transactions on Ultrasonics, Ferroelectrics, and Frequency Control; vol. 48, No. 4; Jul. 2001; pp. 886-894.
A New Method for Estimation of Velocity Vectors; Jorgen Arendt Jensen; IEEE Transactions on Ultrasonics, Ferroelectrics, and Frequency Control; vol. 45, No. 3; May 1998; pp. 837-851.
Comparison of Parabolic and Gaussian Lateral Cosine Modulations in Ultrasound Imaging, Displacement Vector Measurement, and Elasticity Measurement; Chikayoshi Sumi et al.; Japanese Journal of Applied Physics; vol. 47, No. 5, 2008; pp. 4137-4144.
Displacement Vector Measurement Using Instantaneous Ultrasound Signal Phase—Multidimensional Autocorrelation and Doppler Methods; Chikayoshi Sumi; IEEE Transactions on Ultrasonics, Ferroelectrics, and Frequency Control; vol. 55(1); Jan. 2008; pp. 24-43.
Effective Lateral Modulations With Applications to Shear Modulus Reconstruction Using Displacement Vector Measurement; Chikayoshi Sumi et al.; IEEE Transactions on Ultrasonics, Ferroelectrics, and Frequency Control; vol. 55, No. Dec. 2008; pp. 2607-2625.
Efficient Synthetic Aperture Imaging from a Circular Aperture with Possible Application to Catheter-Based Imaging; Matthew O'Donnell et al.; IEEE Transactions on Ultrasonics, Ferroelectrics, and Frequency Control; vol. 39, No. 3; May 1992; pp. 366-380.
Fine Elasticity Imaging Utilizing the Iterative RF-echo Phase Matching Method; Chikayoshi Sumi; IEEE Transactions on Ultrasonics, Ferroelectrics, and Frequency Control; vol. 46, No. 1; Jan. 1999, pp. 158-166.
Increasing Accuracy of Tissue Shear Modulus Reconstruction Using Ultrasonic Strain Tensor Measurement Lateral Modulation and Regularization; C. Sumi; Acoustical Imaging; pp. 59-68.
Japanese Office Action dated Jul. 16, 2013 in counterpart Japanese Application No. 2010-144921.
Martin E. Anderson, "Multi-Dimensional Velocity Estimation with Ultrasound Using Spatial Quadrature", IEEE Transactions on Ultrasonics, Ferroelectrics, and Frequency Control, May 1998, vol. 45, No. 3, pp. 852-861.
Multi-Dimensional Velocity Estimation with Ultrasound Using Spatial Quadrature; Martin E. Anderson; IEEE Transactions on Ultrasonics, Ferroelectrics, and Frequency Control; vol. 45, No. 3; May 1998; pp. 852-861.
Phantom Experiment on Estimation of Shear Modulus Distribution in Soft Tissue from Ultrasonic Measurement of Displacement Vector Field; Chikayoshi Sumi et al.; IEICE Trans. Fundamentals; vol. E78-A, No. 12; Dec. 12, 1995; pp. 1655-1664.

(56) References Cited

OTHER PUBLICATIONS

Real-Time 3-D Ultrasound Imaging Using Sparse Synthetic Aperture Beamforming; Geoffrey R. Lockwood et al.; IEEE Transactions on Ultrasonics, Ferroelectrics, and Frequency Control; vol. 45, No. 4; Jul. 1998; pp. 980-988.

Spatial Inhomogeneity of Tissue Thermal Parameter of Ebbini's Model and Its Dependency on Temperature; Chokayoshi Sumi et al.; Japanese Journal of Applied Physics; vol. 46, No. 7B; 2007; pp. 4790-4792.

Sumi, "Utilization of an ultrasound beam steering angle for measurements of tissue displacement vector and lateral displacement", Reports in Medical Imaging, vol. 3, Sep. 13, 2010, pp. 61-81.

Sumi, "Displacement Vector Measurement Using Instantaneous Ultrasound Signal Phase—Multidimensional Autocorrelation and Doppler Methods", IEEE Transactions on Ultrasonics, Ferroelectrics, and Frequency Control, Jan. 2008, vol. 55, No. 1, pp. 24-43.

Synthetic Aperture Imaging for Small Scale Systems; Mustafa Karaman et al.; IEEE Transactions on Ultrasonics, Ferroelectrics, and Frequency Control; vol. 42, No. 3; May 1995; pp. 429-442.

Synthetic Aperture Techniques with a Virtual Source Element; Catherine H. Frazier et al.; IEEE Transactions on Ultrasonics, Ferroelectrics and Frequency Control; vol. 45, No. 1; Jan. 1998; pp. 196-207.

Xunchang Chen, et al., "Lateral Speckle Tracking Using Synthetic Lateral Phase", IEEE Transactions on Ultrasonics, Ferroelectrics, and Frequency Control, vol. 51, No. 5, May 2004, pp. 540-550.

* cited by examiner

ULTRASOUND BEAM (a) ULTRASOUND ELEMENT (b) ONE-DIMENSIONAL ULTRASOUND ELEMENT ARRAY (c) TWO-DIMENSIONAL ULTRASOUND ELEMENT ARRAY (a) ULTRASOUND BEAM (b) ULTRASOUND BEAM (a)

(b)　　　　　　　　(c)

(a)

(b)

(c)

DISPLACEMENT MEASUREMENT METHOD AND APPARATUS, AND ULTRASONIC DIAGNOSTIC APPARATUS

CROSS-REFERENCE TO RELATED APPLICATION

The present application is a Divisional application of U.S. application Ser. No. 12/833,072, filed on Jul. 9, 2010, and which claims priority from Japanese Patent Application Nos. 2009-209656, filed on Sep. 10, 2009, and 2010-144921, filed on Jun. 25, 2010. The contents of all of the above-identified applications are incorporated herein by reference in their entirety.

BACKGROUND OF THE INVENTION

Field of the Invention

The present invention describes displacement measurement methods and displacement measurement equipments that allow non-destructive and quantitative measurements of internal mechanical properties or internal physical quantities such as a displacement, a strain, a velocity, an acceleration etc in various objects, structures, substances, materials, living tissues etc. For instance, the present invention includes methods and equipments that generate an ultrasound echo by performing a proper beamforming such that at least one internal distribution of a displacement vector, a strain tensor, a strain rate tensor, a velocity vector and an acceleration vector can be measured. Such physical quantities are generated by a mechanical source such as an external pressure, an external vibration, a radiation force etc. The methods and equipments can also deal with tissues that move spontaneously such as a heart and a lung etc or moved by a body motion, a respiratory, a heart motion, a pulsation etc. Also those can also deal with a blood flow in a heart or a blood vessel. A contrast medium can also be used. Simultaneous measurements of such a tissue motion and a blood flow can also be performed. The results measured can be applied widely, for instance, to measurements of mechanical properties and thermal properties.

A medical field is a typical field to which the present invention is applied, such as ultrasonic diagnosis equipments, magnetic resonance imaging equipments, optical diagnosis equipments etc and radiotherapies etc. That is, for instance, deformability and motion-ability of tissues and blood can be examined for diagnoses. Otherwise, by performing a tracking of a target tissue motion, the safety, reliability and efficiency of various treatments can be increased. Degeneration can also be monitored for confirming a treatment effectiveness of a region of interest (ROI). Application of the present invention is not limited to these. For instance, as non-destructive measurement methods, the evaluations, examinations and diagnoses can be performed for various objects.

Description of a Related Art

For instance, in a medical field, treatments of diseases are performed by a radiotherapy, applications of a high intensity focus ultrasound, a leaser, an electromagnetic radio frequency wave or a microwave, a cryotherapy, or a cooling therapy etc. In these cases, an above-mentioned tracking and a non-invasive monitoring of the treatment effectiveness can be performed. Also an effectiveness of a medicine such as an anti-cancer drug can be performed non-invasively. For instance, the treatment effectiveness can be monitored by non-invasively measuring the degeneration and temperature change generated by radiotherapies. Otherwise, the observation of blood flow in a lesion allows the differentiation of the progress of disease. In order to perform a diagnosis and observe a treatment effectiveness, a tissue characterization can also be performed by evaluating an elastic constant etc after the measurements of displacement, strain and their spatial and temporal changes etc generated by forces applied in a lesion and a treated part.

It is well known that the temperature of a tissue has correlations with the elastic constants, visco-elastic constants, a delay time and a relaxation time with respect the constants, a density etc. Then, by performing non-destructive measurements of elastic constants such as a shear modulus and a bulk-modulus etc, visco-elastic constants such as a visco-shear modulus and a visco-bulk modulus etc, a time delay and a relaxation time with respect the moduli, a density etc, the temperature of a point of interest (POI) and the temperature distribution in an ROI can be measured. The temperature can also be estimated from the strains measured generated by a temperature change. Such temperature measurements allow the monitoring of thermal treatments and the prediction of a temperature distribution to be generated for a planning of the thermal treatments.

An ultrasound diagnosis equipment used in a medical field uses an ultrasound transducer for transmitting an ultrasound into a tissue and receiving ultrasound echo signals generated in the tissue by a reflection or scattering. The received echo signals are converted into an ultrasound image observable, which exhibits a distribution of tissues. Then, the measurements of tissue displacement (vector) generated by an arbitrary mechanical source, tissue strain (tensor) generated, elastic constants etc using such an equipment allows the non-invasive observation of the differences between a lesion and a normal tissue.

At past, for the displacement distribution measurement, the change of echo signals obtained by transmitting ultrasound at different phases (plural phases or times) is observed. From the measured displacement, the strains etc is estimated. Concretely, it is proposed that three, two or one-dimensional ROI is set in a target tissue, and a distribution of three, two or one component of a three dimensional displacement vector is measured. Then, elastic constants etc in ROIs are evaluated from the measured displacements, strains etc.

The transducer is a sensor of a displacement or strain measurement. Instead of the ultrasound transducer, other known transducers such as electromagnetic sensors, light sensors, laser sensors can also be used. The sensor is a contact type or non-contact type. For a mechanical source that yields a displacement or a deformation, the ultrasound transducer itself can also be used as a static compressor. The transducer can also be used as a vibrator by assembling a mechanical vibration function into the transducer contact surface. Also others from the transducer, a compressor or a vibrator can be used. A heart motion or a pulsation can also be used (i.e., internal mechanical sources). Also a radiated ultrasound or vibration from a transducer can be used as a mechanical source to yield a deformation in an ROI. The transducer can work as a sensor as well. For the tissue characterization, change in elastic constants, temperatures, thermal properties etc generated by a treatment can also be used.

However, in the most classical fashion, a tissue displacement is measured by applying a one-dimensional signal processing to the ultrasound echo signals under the assumption that the target tissue moves in the same direction as that of the ultrasound beam. Therefore, when the target tissue displacement (motion) has a lateral component (component of the orthogonal direction to the beam direction), the measurement accuracy of the beam direction (axial direction) becomes low (ref. 1: C. Sumi et al, "Phantom experiment on estimation of shear modulus distribution in soft tissue from ultrasonic measurement of displacement vector field", IEICE Trans. on Fundamental, vol. E78-A, no. 12, pp. 1655-1664, December 1995). Here, the ultrasound echo signals involve a raw echo signal, an analytic signal, a quadrate detection, and an envelope detection etc. It is also impossible to measure the lateral displacement component. Therefore, there exists a limitation for the measurement accuracy of the blood flow in a heart and a blood vessel running parallel to the body surface. In addition, it is also difficult to deal with a part of which deformation cannot be controlled externally and a tissue deforms spontaneously by the internal mechanical sources such as a heart etc (for instance, a liver).

Alternatively, the present inventor proposes a displacement vector measurement method that yields the vector measurement from the gradient of the phase of local multidimensional (three- or two-dimensional) cross-spectrum of echo signals (multidimensional cross-spectrum phase gradient method). The cross-correlation method can also be used (refs. 1 and 2: C. Sumi, "Fine elasticity imaging on utilizing the iterative rf-echo phase matching method," IEEE Trans. on Ultrasonics, Ferroelectrics and Frequency Control, vol. 46, no. 1, pp. 158-166, January 1999, etc). The present inventor also propose a multidimensional autocorrelation method and multidimensional Doppler method that deal with multidimensional analytic signals (ref. 3: C. Sumi, "Digital measurement method of tissue displacement vector from instantaneous phase of ultrasonic echo signal," Technical report of Japan Society of Ultrasound Medicine, pp. 37-40, December 2002, Tokyo, Japan (in Japanese) orC. Sumi, "Displacement vector measurement using instantaneous ultrasound signal phase—Multidimensional autocorrelation and Doppler methods," IEEE Trans. on Ultrasonics, Ferroelectrics and Frequency Control, vol. 55, pp. 24-43, January 2008, etc). These measurement methods are properly used or properly combined according to the application of the measurement, specifically, according to the measurement accuracy and calculation time required.

For the displacement vector measurement, the multidimensional phase matching method which the present inventor previously invented is effective (refs. 1 to 3). The phase matching is performed in a multidimensional space (a three-dimensional space is expressed using axial, lateral and elevation directions; a two-dimensional region is expressed using axial and lateral directions) for the same paired echo signals by rotating a phase of the 1st or 2nd echo signals in an analogue manner using the measured displacements, or by spatially shifting the local echo signals using the approximated displacement components as a multiplication of the corresponding sampling intervals by truncating or round off. The phase matching prevents the measurement from suffering an aliasing due to a large displacement in a beam direction. Also the phase matching increases a measurement accuracy of all the displacement components (i.e. all directions) by increasing a correlation and/or coherence between the echo signals. For instance, coarse measurements obtained by the multidimensional cross-correlation method or the multidimensional cross-spectrum phase gradient method are used to perform a coarse phase matching. After the coarse phase matching, the multidimensional cross-spectrum phase gradient method, the multidimensional autocorrelation method or the multidimensional Doppler method is used to yield a fine measurement. Otherwise, after the coarse phase matching, the corresponding one-dimensional methods can also be applied to yield only an axial displacement measurement or a displacement vector components, although the measurement accuracy is lower than that obtained by the multidimensional methods (ref. 3).

By performing the phase matching, even if an uncontrollable mechanical source exists in an ROI (heart motion, respiratory, blood vessel pulsation, body motion etc), it is also possible to measure a displacement vector or an axial displacement. Thus, the phase matching allows yielding the useful measurement absolutely. The multidimensional vector measurement methods also yield results in a real-time similarly to the corresponding one-dimensional methods.

However, even if the phase matching is performed, the measurement accuracy of the axial displacement becomes low when using the one-dimensional displacement measurement method. This is because the residual lateral displacement exists. Thus, the measurement accuracy depends on the accuracy of the coarse phase matching. When using a conventional ultrasound equipment for the displacement vector measurement, the accuracy and spatial resolution of the measured lateral displacement are low, because the lateral carrier frequency does not exist and the lateral bandwidth is smaller than the axial one. Thus, the measurement accuracy of a displacement vector and a strain tensor becomes low, being dependent of the measurement accuracy of the lateral displacement.

Then, the present inventor realized a remarkably accurate displacement vector measurement on the basis of the above-mentioned displacement vector measurement methods, however, with a use of echo signals having lateral and elevational carrier frequencies. Such a use of echo signals allows the increase in a measurement accuracy of an axial displacement. It is referred to as a lateral modulation we called (refs. 3 and 4: C. Sumi et al, "Effective lateral modulations with applications to shear modulus reconstruction using displacement vector measurement," IEEE Trans. on Ultrasonics, Ferroelectrics and Frequency Control, vol. 55, pp. 2607-2625, December 2008; ref. 5: C. Sumi et al, "Comparison of parabolic and Gaussian lateral cosine modulations in ultrasound imaging, displacement vector measurement, and elasticity measurement", Jpn, J. Appl. Phys., vol. 47(5B), pp. 4137-4144, May 2008 etc). For the lateral modulation, J. A. Jensen et al and M. E. Anderson determined an apodization function to be used using the Fraunhofer approximation (ref. 6: J. A. Jensen, "A new method for estimation of velocity vectors", IEEE Trans. Ultrason., Ferroelect., Freq. Contr., vol. 45, pp. 837-851, 1998; ref. 7: M. E. Anderson, "multi-dimensional velocity estimation with ultrasound using spatial quadrature", IEEE Trans. Ultrason., Ferroelect., Freq. Contr., vol. 45, pp. 852-861, 1998), whereas the present inventor determines the apodization function using the optimization method developed (ref. 8: C. Sumi et al, "A demonstration of optimal apodization determination for proper lateral modulation", Jpn, J. Appl. Phys., vol. 48(7B), July 2009, etc).

For the beamforming of a lateral modulation, the present inventor realized various useful methods on the basis the use of crossed, steered beams (i.e., not the Fraunhofer approximation, ref. 4): using a classical monostatic or multistatic synthetic aperture (SA) method; transmitting crossed beams simultaneously and receiving crossed beams simultaneously; transmitting crossed plane beams for a wide region and superposing generated echo beams; using such crossed beams, however, transmitted or received using different or plural physical apertures; using such crossed beams, however, generated at different phases.

The lateral modulation developed by the present inventor can be realized by achieving crossed beams using steered beams in arbitrary directions. Then, arbitrary type transducers such as a linear array type transducer can be used, i.e., arbitrary coordinate systems can be used. In such coordinate systems, crossed beams can be generated using steered beams having arbitrary directions. Thus, the crossed beams are not always symmetric in a lateral direction. Such a non-symmetric beamforming is effective when the obstacles such as a bone exist, for instance. Non-steered beam can also be used as one beam of crossed beams. Mechanical steering can also be used together. At a point of interest (POI), a steering angle or crossed angle of steered beams should be large. Although the lateral modulation can be performed with a consideration about the apodization (beam shape), the apodization optimized by the present inventor allows yielding a lateral modulation with a wide lateral bandwidth. This increases the spatial resolution of ultrasound image obtained and the measurement accuracy of a displacement vector measurement achieved.

For the lateral modulation (ref. 3), to obtain a three-dimensional echo data frame (i.e., three-dimensional displacement vector measurement), crossed beams must be generated using four or three steered beams, whereas to obtain two-dimensional echo data frame (i.e., two-dimensional displacement vector measurement), crossed beams must be generated using two steered beams. In the present invention, similarly to a conventional case, the respective three- or two-dimensional frames generated are approximated as echo data frames that exhibit a tissue distribution at respective time phases, although it takes a finite time to receive all echo signals and generate the respective frames. The inversion of the time difference between the frames obtained is called as a frame rate. Due to the existence of a tissue motion, the time required to generate one frame should be short. Hereafter, the time phase is referred to as defined here.

For the lateral modulation, however, larger number of beams must be generated than the conventional beamforming. Then, it may take a longer time to obtain echo signals and achieve the signal processing such as the apodization, switching, implementation of delay on echo signals, phase matching on echo signals, summation of echo signals. Then, the frame late may become lower than the conventional imaging. When using a classical synthetic aperture (SA), the echo signal-to-noise ratio (SNR) obtained will be low, because the transmitted ultrasound powers from the respective elements are small. In addition, particularly when dealing with deeply situated tissues, a larger physical aperture is required than that for a conventional beamforming. The field of vision (FOV) obtained may become smaller in lateral and elevational directions than that for a conventional beamforming.

Alternatively, an accurate displacement vector measurement can be achieved by synthesizing the accurately measured axial displacements obtained from respective steered beams with the same steering angle (ref. 3), i.e., the superposition is not performed. However, the frame rate may become low similarly to the lateral modulation. When using steered beams obtained at different phases, the tissue displacement between the two frames obtained leads to a measurement error.

SUMMARY OF THE INVENTION

The purpose of the present invention is that an accurate real-time measurement of a displacement vector or a one-directional displacement is achieved on the basis of the proper beamforming that require a short time for obtaining one echo data frame without suffering affections by a tissue motion.

In order to achieve the above-mentioned purpose, a displacement measurement method according to one aspect of the present invention includes the steps of:

(a) yielding ultrasound echo data frames by scanning an object laterally or elevationally using an ultrasound beam steered electrically and/or mechanically with a single steering angle over an arbitrary three-dimensional orthogonal coordinate system involving existence of three axes of a depth direction, a lateral direction, and an elevational direction or an arbitrary two-dimensional orthogonal coordinate system involving existence of two axes of a depth direction and a lateral direction; and (b) calculating a displacement vector distribution by implementing a predetermined block matching on the ultrasound echo data frames yielded at more than two phases.

Further, a displacement measurement apparatus according to one aspect of the present invention includes:

at least one ultrasound sensor for transmitting ultrasounds to an object in accordance with at least one drive signal, and detecting ultrasound echo signals generated in the object to output echo signals;

driving and processing means for supplying the at least one drive signal to the sensor, and processing the echo signals outputted from the sensor;

control means for controlling respective means to yield ultrasound echo data frames by scanning an object laterally or elevationally using an ultrasound beam steered electrically and/or mechanically with a single steering angle over an arbitrary three-dimensional orthogonal coordinate system involving existence of three axes of a depth direction, lateral direction, and an elevational direction or an arbitrary two-dimensional orthogonal coordinate system involving existence of two axes of a depth direction and a lateral direction; and data processing means for calculating a displacement vector distribution by implementing a predetermined block matching on the ultrasound echo data frames yielded at more than two phases.

The beamforming method according to one aspect of the present invention uses conventional apodization, switching, delay, phase matching, summation and mechanical scanning etc, by which so-called steering beams to be used for scanning the object or target are generated for yielding the echo data frames, however, with the same steering angle (i.e., a single steering angle), for both the transmission and reception over the three-, two- or lateral one-dimensional region of interest (ROI) constructed. By using displacement vector measurement methods, one-directional displacement measurement methods or the combination, a displacement vector, a lateral displacement (one-directional displacement) or the distribution is measured on the basis of the phase difference between the steering beams or echo data frames obtained at different phases. A synthetic aperture can also be used. The one-dimensional ROI is not always lateral, for instance, an axial one-dimensional ROI.

Because the beamforming method does not generate plural steering beams with different steering angles, the beamforming allows the decrease in the errors generated due to the tissue motion during an echo data acquisition. As described later, however, the beamforming does not always yield the most accurate measurement and imaging. Then, the lateral modulation described above and the conventional beamforming (non-steering) can also be chosen as a beamforming method together with a displacement measurement method. As described later, a mechanical scan can also be performed. When performing the displacement measurement after one of the beamformings, as described later, the coordinate system can be rotated to increase the measurement accuracy. In a frequency domain, as described later, spectra division or frequency division referred to as can also be performed. The ultrasound apparatus related to the present invention is equipped with such beamformings, displacement measurement methods and function for automatically or manually choosing or combining the beamformings and displacement measurement methods. A synthetic aperture can also be performed.

Thus, on the basis of one of viewpoints of the present invention, the combinational use of the prescribed steering beams with a single steering angle (the same steering angle), and the prescribed processings and displacement measurement methods allows providing new real-time measurement methods for a displacement vector, a lateral displacement (one-directional displacement) and the distribution, new displacement measurement apparatuses and new ultrasound diagnosis apparatuses. A synthetic aperture can also be used.

DESCRIPTION OF THE PREFERRED EMBODIMENTS

The following is explanation in detail of conduct forms of the present invention with referring to figures.

Figure 1:
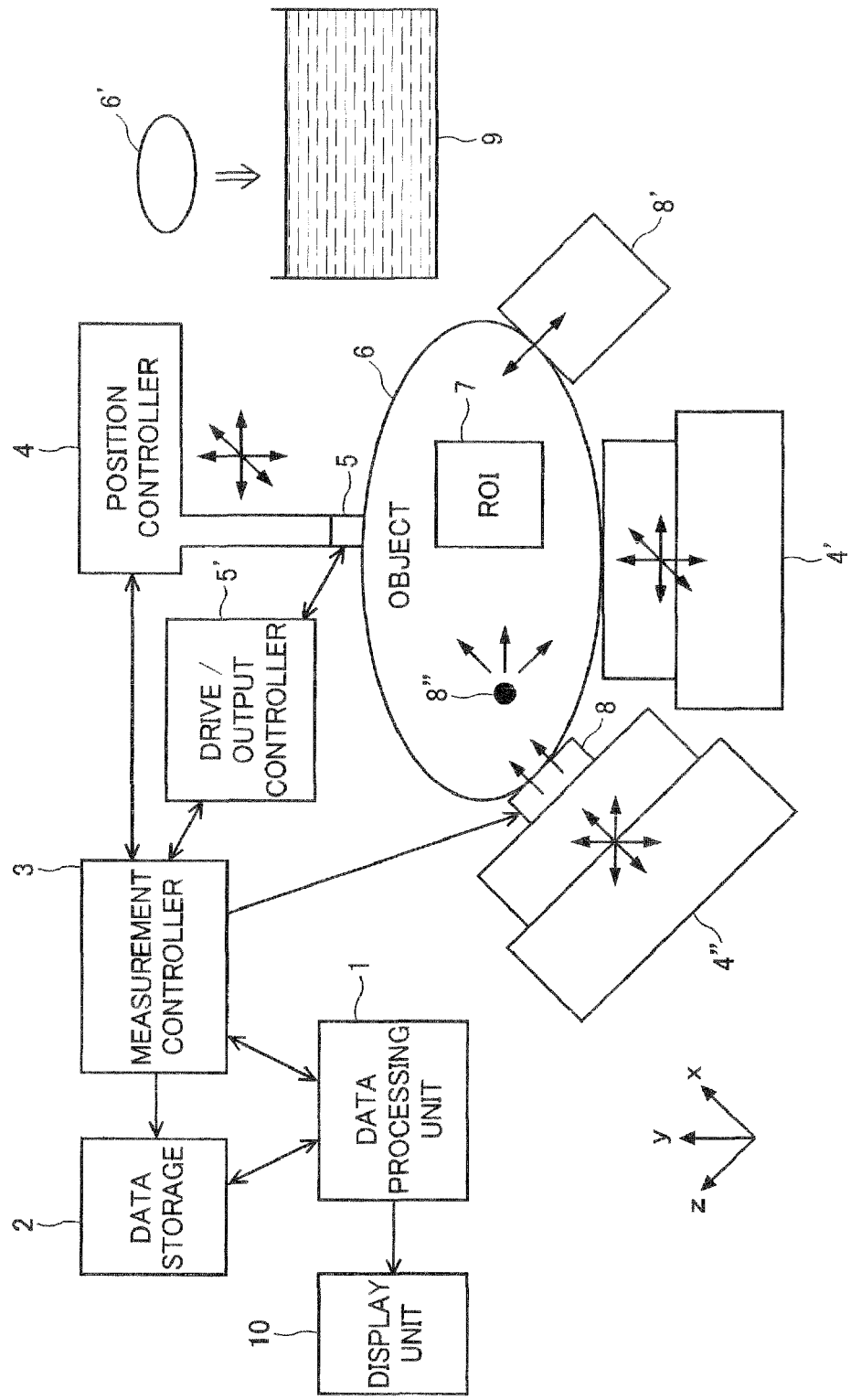
FIG. 1 shows a schematic representation of a global frame of displacement vector measurement apparatus, related to one of conduct forms of the present invention.

FIG. 1 shows a schematic representation of a global frame of a displacement measurement apparatus, related to one of conduct forms of the present invention. This apparatus measures distributions or time series of displacement vector components, strain tensor components and their temporal and/or spatial partial derivatives etc in a three-, two- or lateral one-dimensional ROI 7 set in a measurement object 6 to obtain velocity vector field, acceleration vector field, strain tensor field, strain rate tensor field etc. The one-dimensional ROI is not always lateral, for instance, an axial one-dimensional ROI. From these measurements, this apparatus measures following constant distributions, i.e., elastic constants such as shear modulus, Poisson's ratio etc, visco-elastic constants such as visco-shear modulus, visco-bulk modulus etc, delay times or relaxation times relating these elastic constants and visco-elastic constants, density etc. Using this apparatus, displacement measurement related to one of conduct forms of the present invention is performed. Moreover, using this apparatus, an ultrasound diagnosis apparatus related to one of conduct forms of the present invention is realized.

As shown in FIG. 1, the displacement/strain sensor 5 is directly contacted to the object surface, or a suitable medium is put between the sensor and object. For this conduct form, as the displacement/strain sensor, an ultrasound transducer is used. The transducer may have one- or two-dimensional array of oscillators etc. A single oscillator can also be used. One or plural ultrasound sensors transmit ultrasounds to the object in accordance with one or plural drive signals, and detect ultrasound echo signals generated in the object to output one or plural received echo signals. The transmission beamforming processing forms a transmission ultrasound beam using the ultrasounds transmitted from one or plural ultrasound sensors, whereas the reception beamforming processing forms a reception ultrasound beam using the ultrasounds received by one or plural ultrasound sensors.

The displacement between the displacement/strain sensor 5 and the object 6 can be mechanically controlled using a position controller 4. Moreover, the relative distance between the displacement/strain sensor 5 and the object 6 can be mechanically controlled by a position controller 4'. An ultrasound transmitter or an ultrasound pulser 5' is equipped with to generate one or plural drive signals to drive the displacement/strain sensor 5, and 5' also serves as an output controller, i.e., a receiver with an amplifier of one or plural echo signals detected by the displacement/strain sensor 5. Thus, 5' is a drive/output controller. Furthermore, mechanical sources 8 and 8' can be equipped with to actively apply static compressions and vibrations, respectively, together with a mechanical position controller 4". For the mechanical source, the ultrasound sensor can also be as a compressor or vibrator. A heart motion and a pulsation can also be used as a mechanical source 8".

The echo signals output from the drive/output controller 5' are stored at a data storage 2 through a measurement controller 3. Therefore, the drive/output controller 5' may have an analogue-to-digital (AD) converter inside or outside. As described specifically later, the drive/output controller 5' can also perform a reception beamforming as well as a transmission beamforming. Then, an ultrasound echo data frame generated by the reception beamforming may be stored at the data storage 2. Otherwise, the plural received echo signals before performing a reception beamforming may be stored at the data storage 2, after which the stored data are read out by a data processing unit 1. The data processing unit may also perform the reception beamforming, by which an echo data frame may be generated. In this case, the echo data frame generated can be stored at the data storage 2 through the measurement controller 3. For both cases, the command for the displacement measurement is output from the measurement controller 3, displacement vector component distributions or one-directional displacement distribution in an ROI 7 of an arbitrary time, or their time series are calculated from plural echo data frames generated at different phases using the calculation processing described specifically later. Thus, in the former case, the data processing unit 1 performs the displacement calculations after reading out the echo data frames from the data storage 2, whereas in the latter case, the generation of echo data frames (i.e., beamforming) and the displacement calculations can also be performed by the respective processors. The distributions of displacement vector components or one-directional displacement, or their time series calculated may be stored at the data storage 2.

The data processing unit 1 calculates the temporal and/or spatial partial derivatives of the displacement component distributions measured, i.e., strain tensor component distributions (time series), strain rate tensor component distributions (time series), velocity vector component distributions (time series), acceleration vector component distributions (time series). That is, the strain tensor component distributions (time series) are calculated by implementing a 3D, 2D or 1D spatial differential filter to the displacement vector component distributions (time series) obtained. The cut off frequencies of all the filters can be set different values freely at each point and time in each spatial and temporal direction as those of usual filters. The acceleration vector component distributions (time series) are calculated by implementing a time differential filter twice to the measured displacement vector component distributions (time series). The strain rate tensor component distributions (time series) are calculated by implementing a spatial differential filter to the velocity vector component distributions (time series) calculated by implementing a time differential filter to the displacement vector component distributions (time series) obtained, or by implementing a time differential filter once to the strain tensor component distributions (time series) obtained. Moreover, when strain tensor component distributions (time series) are directly calculated of the ROI 7 and obtained, strain rate tensor component distributions (times series) are obtained by implementing time differential filter to the measured strain tensor component distributions (time series).

Furthermore, this data processor 1 calculates following constant distributions, i.e., elastic constants such as shear modulus, Poisson's ratio etc, visco-elastic constants such as visco-shear modulus, visco-bulk modulus etc, delay times or relaxation times relating these elastic constants and visco-elastic constants or density from the calculated distributions of strain tensor components (time series), strain rate tensor components (time series), acceleration vector components (time series) etc. These calculated results are stored at the storage 2.

The measurement controller 3 controls the data processing unit 1, the position controllers 4 and 4", and the drive/output controller 5'. The position controllers 4 and 4' may be a human hand. When the object 6 is spatially fixed, the position controller 4' is not used. When the displacement/strain sensor 5 is an electric scan type, the position controller 4 is not always used. Being dependent of the size of the ROI 7, it may be possible to achieve the measurements without mechanical scanning. The displacement (strain) sensor 5 may be contacted onto the object 6 directly, or may not. For instance, when monitoring the treatment effectiveness of High Intensity Focus Ultrasound (HIFU), the displacement/strain sensor 5 and the object 6' may be dipped in or immersed in a water tank.

Figure 2:
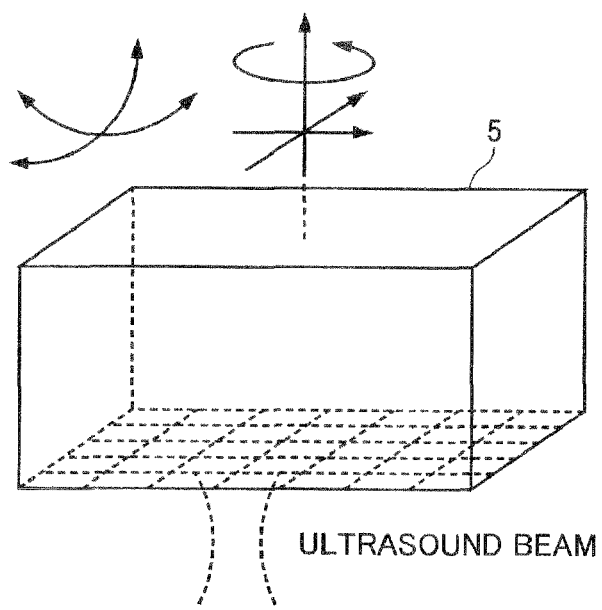
FIG. 2 shows an illustration of mechanical scan movements of a displacement/strain sensor.

FIG. 2 shows an illustration for explaining the mechanical scan using the displacement/strain sensor 5. The mechanical scan includes a mechanical steering. The position controller 4 shown in FIG. 1 controls the relative position between the displacement/strain sensor 5 and the object 6 mechanically. For instance, as shown in FIG. 2, the position controller 4 realizes vertical, horizontal, turn and fan-directional movements. Then, the position controller may by a human hand.

As shown in FIG. 1, the output of the drive/output controller 5' is stored at the data storage 2 successively or with a prescribed interval. The data processing unit 1 controls the drive/output controller 5' and then acquires the echo's basic wave components, n-th harmonic wave components (n from 2 to N) or all the components in three-, two- or one-dimensional ROI 7, and implements the calculation processing described later to yield displacement data, strain data, strain rate data or acceleration data.

As described above, the drive/output controller 5' and the data processing unit 1 obey the commands of the measurement controller 3 to perform the beamforming such as transmission fixed focusing, multi-transmission fixed focusing, reception dynamic focusing etc. Furthermore, an apodization is also performed to sharpen the ultrasound beam, i.e., weighting the ultrasounds transmitted and received at the respective sensors. If necessary, with the steering of the beams, the echo signals from the ROI 7 are acquired.

Figure 3:
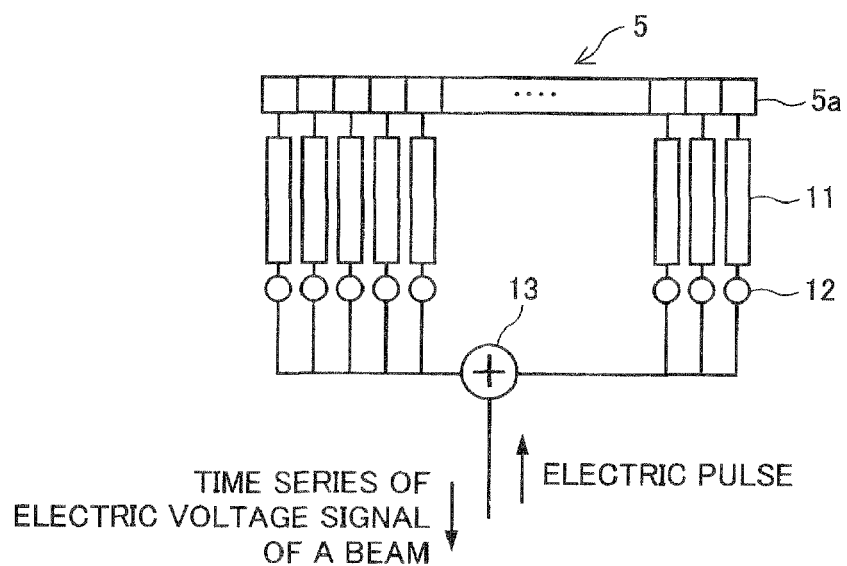
FIG. 3 shows illustrations of compositions for beamforming such as an apodization, a switching, a delay, a phase matching, and a summation processing etc.

FIG. 3 shows illustrations of compositions for beamforming such as an apodization, a switching, a delay, a phase matching, and a summation processing etc. The order of the connections are changeable. For instance, in the case of FIG. 3, the respective oscillators or sensors 5a assembled in the displacement/strain sensor 5 is connected to delay lines 11 and amplifiers etc. The delay lines are connected to apodization units or switches 12. The apodization units are comprised of amplifiers and attenuators etc, whereas the switches make the respective channels on or off. The delay lines 11, and apodization units or switches 12 are controlled by the measurement controller 3 (FIG. 1). The plural apodization units or switches 12 are connected to the summation unit 13.

For the reception of the echo signals, plural echo signals output through the plural sensors 5a, amplifiers, delay lines 11 and apodization units (a kind of calculator can also be used) or switches 12 etc are properly summed by the summation unit 13, by which the reception-focused beams are obtained. The echo data frames are obtained by A/D conversion of the echo signals using the A/D converter. For the transmission of ultrasounds, the drive signals are supplied to the plural sensors 5a through the apodization units or switches 12, delay lines 11, amplifiers etc. All these components may also be realized by the data processing unit 1 or partially by the drive/output controller 5; and the order of the connections and the comprising can also be arranged variously.

For this conduct form, the beam steering with a single steering angle (the same steering angle) is performed. The object 6 is scanned in a lateral direction. However, it is not always that the steering angle is invariant. If possible, the steering angle and crossed angle should be as large as possible. The combinational use of the single aperture and mechanical scan and synthetic aperture can also be performed. For all the beamforming, the received echo signals are properly filtered, amplified and A/D-converted. If necessary, the calculator can also be widely used for the signal processing.

Figure 4:
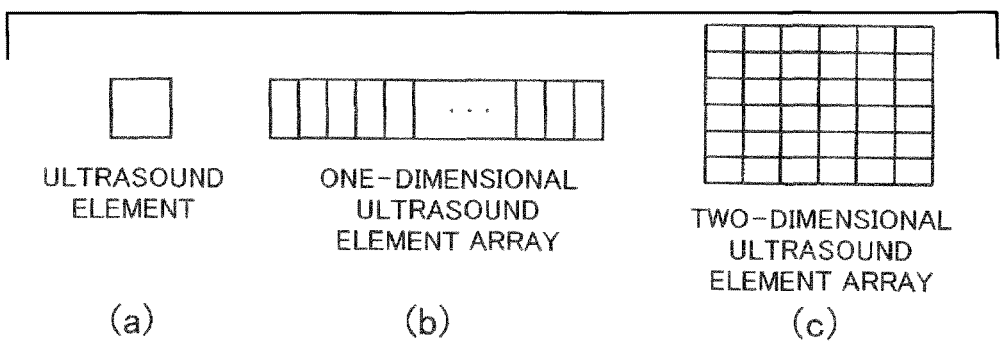
FIG. 4 shows an illustration of a displacement/strain sensor applicable to the present invention.

FIG. 4 shows an illustration of a displacement/strain sensor 5 applicable to the present invention. For this invention, as the displacement/strain sensor 5, the following type ultrasound transducers can be utilized, i.e., a two-dimensional array type being mechanical scan possible, a two-dimensional array type being electronic scan possible, a one-dimensional array type being mechanical scan possible, and a one-dimensional array type being electronic scan possible. Other various type transducer such as a sector-type transducer can also be used. To increase the steering angle, a mechanical scan can also be performed.

Figure 5:
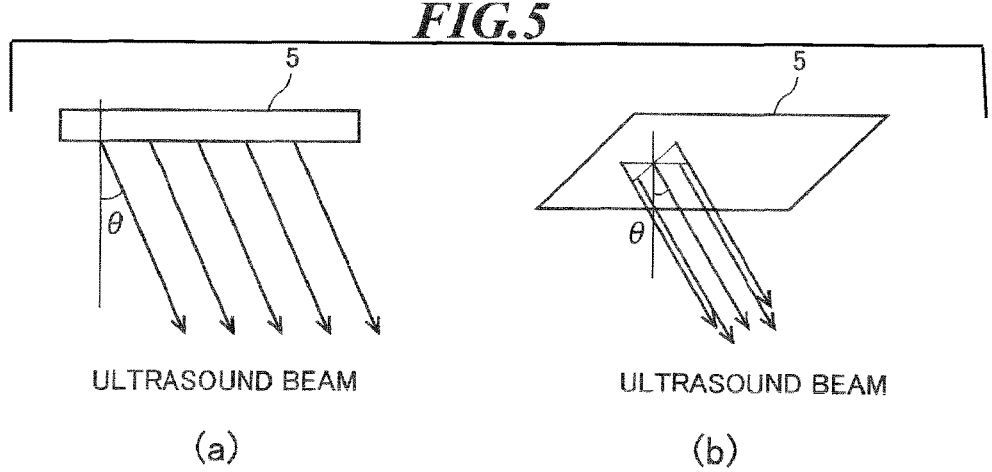
FIG. 5 shows an illustration of a lateral scan using steering beams with a single steering angle (the same steering angle)
Figure 6:
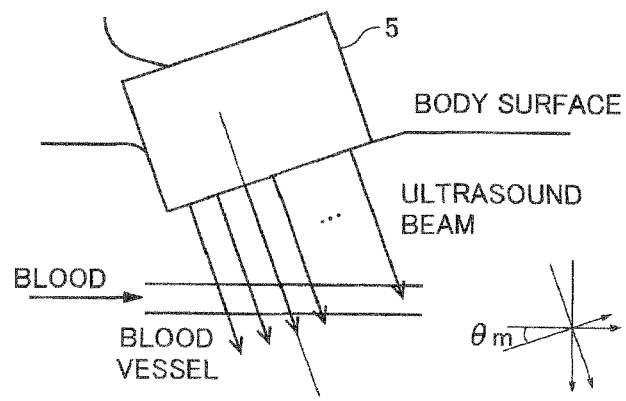
FIG. 6 shows an illustration of a case of beam steering using a mechanical scan.

FIG. 5 shows an illustration of a lateral scan using steering beams with a single steering angle (the same steering angle), in which θ expresses the steering angle (0°<θ<90°. FIG. 5a shows a scan of a two-dimensional region using a one-dimensional array, whereas FIG. 5b shows a scan of a three-dimensional region using a two-dimensional array. FIG. 6 shows a mechanical steering, in which θm shows the steering angle (0°<θm<90°). When generating the echo data frame or after generating the frame, a proper three-dimensional orthogonal coordinate system involving the existence of three axes of a depth direction, and the lateral and elevational directions or a proper two-dimensional orthogonal coordinate system involving the existence of two axes of a depth direction and the lateral direction is formed.

For this conduct form, the beam steering with a steering angle is performed as described in paragraphs 0035 to 0037 (FIG. 5). As described in the paragraphs 0035 to 0037, the beam steering can be performed using the electric beamforming such as the apodization, switching, delay, phase matching, summation processing etc. Also as described in the paragraph 0033, the mechanical scan (FIGS. 2 and 6) can also be performed by slanting the displacement/strain sensor 5. A synthetic aperture can also be performed.

For the case using the electric steering, when generating the steering beams, an arbitrary three-dimensional orthogonal coordinate system involving the existence of three axes of a depth direction, and the lateral and elevational directions or an arbitrary two-dimensional orthogonal coordinate system involving the existence of two axes of a depth direction and the lateral direction is formed. When the target tissue moves in a lateral direction dominantly, not a displacement vector measurement but a one-dimensional displacement measurement described specifically later is also applicable. In such a case, in order to increase the measurement accuracy, the coordinate system is set such that not an axial direction but a lateral direction corresponds to the direction of the target motion. In such a case, the mechanical scan may also be performed by slanting the displacement/strain sensor 5. Such a lateral one-dimensional displacement measurement does not lead to the measurement errors (described above) caused when using the conventional axial one-dimensional displacement measurement used under the condition that the beam direction cannot set in the direction of the target motion. Similarly to the lateral modulation (LM), the configurations of the displacement/strain sensor 5 and the object become simple and the measurement accuracy achieved also becomes high. When the target tissue dominantly moves in the depth direction, the one-dimensional displacement measurement should be performed under the condition that the beam direction corresponds to the depth direction. That is, either axial or lateral axis should be chosen such that easily the axis can be set in such a proper way. The beam steering should be performed such that the beam is steered in the direction of the target motion. Then, if necessary, the mechanical scan may also be performed by slanting the displacement/strain sensor 5. However, the one-dimensional displacement measurement should used for the measurement of a lateral displacement. A synthetic aperture may also be performed. Although the one-dimensional displacement measurement is referred to as using "one-dimensional," as is well known, multidimensional signal processings are used for stabilizing the measurement and increasing the measurement accuracy, for instance, for a moving-average of a phase difference etc. The "One-dimension" means the dimension of the target displacement, i.e., one-direction. The one-dimensional displacement measurement can also be referred to as the one-directional displacement measurement.

When performing the mechanical beam steering, the displacement/strain sensor 5 is slanted with respect to the object by the mechanical scanning (FIG. 6). In such a case, the mechanical steering angle θm shown in FIG. 6 is sensed, which is used for forming a three-dimensional orthogonal coordinate system involving the existence of three axes of a depth direction, and the lateral and elevational directions or a two-dimensional orthogonal coordinate system involving the existence of two axes of a depth direction and the lateral direction. Alternatively, after beamforming using a three- or two-dimensional orthogonal coordinate system without using the mechanical steering angle θm, the coordinate system is rotated using the mechanical steering angle θm such that the same coordinate system having an axis of a depth direction at least (FIG. 6). In such a case, the steered beam data digitized by A/D conversion are interpolated to obtain the data over the coordinate system reformed. A synthetic aperture may also be used together.

In such a case, if the target tissue moves in a lateral direction dominantly, not a displacement vector measurement but a lateral one-dimensional displacement measurement described specifically later is applicable. In such a case, in order to increase the measurement accuracy, the coordinate system is set such that not an axial direction but a lateral direction corresponds to the direction of the target motion. When the target tissue dominantly moves in the depth direction, the one-dimensional displacement measurement should be performed under the condition that the beam direction corresponds to the depth direction. That is, either axial or lateral axis should be chosen such that easily the axis can be set in such a proper way. The beam steering should be performed such that the beam is steered in the direction of the target motion. Strictly, the interpolation processing should be performed using the above-described phase matching on the basis of the Nyquist theorem (see ref. 1: The value at the desired position is obtained by spatially shifting the echo data by multiplying a complex exponential expressed using the spatial shift to be realized to the Fourier's transform of the echo data). However, the other interpolations such as the linear interpolation etc can also be performed as the approximate interpolations. A synthetic aperture can also be used together.

For the measurement of spatial displacement distributions, the object is scanned using a steering beam with a single steering angle. For the scanning, the direction of the scanning should correspond to that of the lateral direction of the coordinate system to be used finally. It is absolutely required that every sampling point in the ROI has a steering angle not equal to zero at least (For the lateral modulation, crossed beams are required at each point). For instance, when using a convex- or sector-type transducer, a single steering angle should be realized with respect to the depth direction (axis) of the orthogonal coordinate system that is determined by the curvature of the aperture used. The object should be scanned in the lateral direction (axis) simultaneously set. A synthetic aperture can also be performed. Otherwise, a steering beam with a single steering angle is used over an arbitrary orthogonal coordinate system because an arbitrary shape beam can be tried to be steered in an arbitrary direction within a limitation regardless the aperture geometry by beamforming on the basis the delay, phase matching, summation and apodization or virtual source and receiver described later. Generally, the error of the steering angle with respect to the desired one leads to the measurement error, the displacement measurement methods used or of the present inventions are robust to such an error.

The data processing unit 1 shown in FIG. 1 implement proper displacement measurement methods on the more than two echo data frames obtained by the beam steering at pre- and post-deformation at least to yield two- or three-dimensional displacement vector components, one-directional displacement, their distributions or their time series. If necessary, the mirror setting of echo data is also performed as described specifically later. For the displacement vector measurement, multidimensional displacement vector measurement methods on the basis of a block matching can be used, for instance. In such a case, the mirror setting is not required. Although the block matching methods can also be used for the measurement of a one-directional displacement, multidimensional displacement vector measurement methods with the mirror setting but no block matching yields more accurate measurements. Together with the one-dimensional displacement measurement methods, the one-directional displacement measurement methods described specifically later can also be used for the one-directional displacement measurement, concretely, lateral one-directional displacement measurement methods. However, these one-dimensional and one-directional measurement methods yield lower measurement accuracy than the corresponding multidimensional displacement vector measurement methods even though the multidimensional signal processing is performed such as a moving average.

The data processing unit 1 can also perform an echo imaging by implementing the mirror setting on the echo data frame obtained by the beam steering with a single steering angle. By the processing, quasi-lateral modulation can be performed locally, i.e., superimposition of the mirrored local echo data. When performing a lateral modulation, the one-dimensional and one-directional displacement measurement methods can be used by implementing a demodulation. For the demodulation, several methods have been reported, for instance, ref. 9, J. A. Jensen, "A new estimator for vector velocity estimation," IEEE Trans. Ultrason., Ferroelect., Freq. Contr., vol. 48, pp. 886-894, 2001; and ref. 10, M. E. Anderson, "A heterodyning demodulation technique for spatial quadrature," in 2000 IEEE Ultrasonics Symposium etc. With respect to these, a more simple demodulation method of the present invention will be described later.

Here, it is recalled that for these measurement methods for the multidimensional displacement vector and one-directional displacement allows the measurements by using the phase of the ultrasound echo signals obtained at more than two phases (i.e., different times).

The data processing unit 1 also calculates strain tensor components, strain rate tensor components, acceleration vector components, velocity vector components, their distributions and their time series by implementing spatial and temporal differential filters on the measured displacement vector components, their distributions and their time series.

For the purposes, in order to increase the measurement accuracy of the displacement in the scanning direction, the carrier frequency of the scanning direction should be made as large as possible by increasing the above-described electric and mechanical steering angles, i.e., $\theta$ in FIG. 5 and $\theta m$ in FIG. 6, for instance, $\theta \cong 45°$ and $\theta m \cong 45°$, if possible. However, the steering angle may not be large enough because a large steering angle decreases the SNR of echo signals. Thus, if necessary, the electric steering may performed with the combination of the mechanical steering. A synthetic aperture may also be performed.

The carrier frequency of the scanning direction should be large. In accordance, the beam pitch should be small such that the aliasing does not occur. That is, the carrier frequency cannot become larger than the highest frequency determined by the beam pitch $\Delta y$ on the basis of the sampling theorem, i.e., $1/(2\Delta y)$. However, by making the electric steering angle large, the side lobes and grating lobes grow significantly, all the lobes are tried to be removed in a frequency domain. A synthetic aperture may also be performed.

However, when it is possible to achieve a higher frequency than the highest frequency obtained by the beam pitch realized (Nyquist theorem) by making the steering angle large, the data processing unit 1 widens a lateral bandwidth by padding zero spectra in higher frequencies than the Nyquist frequency (interpolations of lateral sampling points of a coordinate system). In a spatial domain, the number of means can be increased by the spatial interpolations. At the moment of the beamforming, the number of beams can also be increased. In contrary, when a high carrier frequency cannot be obtained, the data processing unit can rotate the coordinate system of the echo data frame. However, the beams should be steered in the direction of the target motion. Recall the measurement case of the blood flow (displacement, velocity etc) in a vessel running parallel to the body surface (FIG. 6). A synthetic aperture can also be used together.

For the purposes, a fundamental wave, or harmonic waves of which higher axial carrier frequency and larger lateral bandwidth respectively increase the measurement accuracy of the axial and lateral displacements, or all waves of which total single-to-noise ratio may be larger than that of the harmonic wave solo are properly used.

That is, the echo imaging is performed using an ultrasound echo signal itself, a fundamental wave extracted (n=1) solo, one of harmonic waves extracted (n=2 to N) solo, or combinations of them. Moreover, the measurement of a displacement vector or a one-directional displacement (mainly, lateral one) is performed.

As described above, the displacement measurement apparatus related to the present conduct form allows the measurements of displacement vector components (distributions, time series), a one-directional displacement (distribution, time series), strain tensor components (distributions, time series), strain rate tensor components (distributions, series), acceleration vector components (distributions, series), velocity vector components (distributions, series) etc using the ultrasound echo data frame measured over the three-, two- or lateral one-dimensional ROI in the object. The apparatus is comprising, the displacement/strain sensor 5 (the ultrasound transducer); mechanical controller 4 of relative position, and vertical, horizontal, turn and fan-directional movements; the drive/output controller 5' for generating drive signals to drive the displacement/strain sensor as the ultrasound transmitter or the ultrasound pulser, processing echo signals detected by the displacement/strain sensor as the receiver with an amplifier; the drive/output controller 5' or the data processing unit 1 for beamforming such as the prescribed beam steering (focusing such as transmission fixed focusing/reception dynamic focusing, transmission multiple focusing/reception dynamic focusing; apodization for sharpening the beam shape); the data storage 2 for storing the output of the displacement/strain sensor. For the synthetic aperture processing, the data storage 2 and the data processing unit 1 work mainly after the A/D conversion.

The data processing unit 1 also works for calculating the displacement vector components (distributions, time series), one-directional displacement (distribution, time series), strain tensor components (distributions, time series), strain rate tensor components (distributions, series), acceleration vector components (distributions, series), velocity vector components (distributions, series) etc, whereas the data storage 2 also stores the calculated results. For echo data acquisition, a mechanical scan can be combined with the electric steering.

The data processing unit 1 will also calculate the strain tensor components (distributions, time series) by implementing a 3D, 2D or 1D spatial differential filter with a cutoff frequency in a spatial domain or their frequency responses to the measured three- or two-dimensional displacement vector components (distributions, time series) in the three-dimensional ROI, two-dimensional displacement vector components (distributions, time series) in the two-dimensional ROI, one-directional displacement (distribution, time series) in the three-, two- or one-dimensional ROI.

The data processing unit 1 will also calculate the strain rate tensor components (distributions, time series), acceleration vector components (distributions, time series) and velocity vector components (distributions, time series) by implementing the temporal differential filter with a cutoff frequency or the frequency response to the measured time series.

To generate more than one strain tensor field (or one displacement vector field) in the three-, two- or one-dimensional ROI in the object, the compressor or vibrator can also be used as a mechanical source. Otherwise, the spontaneous tissue motion such as a heart motion, a pulsation, a respiratory etc may also become such a mechanical source. Such strain tensor components (distributions, time series) generated are measured.

The displacement/strain sensors (ultrasound transducers) applicable to the present invention are following types, i.e., the single aperture type being mechanical scan possible, the two-dimensional array type being electronic or mechanical scan possible, the one-dimensional array type being electric or mechanical scan possible, and other various types. To increase the steering angle, a mechanical scan can also be performed. Echo data frames are obtained by performing the prescribed beam steering using the sensors. A synthetic aperture may also be performed. The displacement/strain sensor may be contacted onto the object directly, or may not. In such a case, the contact surface of the sensor serves as a compressor or vibrator as a mechanical source. When monitoring the treatment effectiveness of High Intensity Focus Ultrasound (HIFU), the displacement/strain sensor and the object may be dipped in or immersed in a water tank (a non-contact case).

When measuring the elasticity such as strain (s), elastic constant distribution (s) or visco-elastic constant distribution (s), a suitable medium is put as a reference for the measurement between the object and the sensor (mechanical source). Otherwise, such a reference can also be properly assembled in the sensor.

Thus, by performing the prescribed beam steering using such type displacement/strain sensors, the data processing unit calculates three- or two-dimensional displacement vector components (distributions, time series) in the three-dimensional ROI, two-dimensional displacement vector components (distributions, time series) in the two-dimensional ROI, or one-directional displacement (distribution, time series) in the three-, two- or one-dimensional ROI; strain tensor components, strain rate tensor components, acceleration vector components, velocity vector components, their distributions and their time series.

Moreover, in these case, the data processing unit can also calculate the above-described displacement vector components (distributions, time series), velocity vector components (distributions, time series), acceleration vector components (distributions, time series), strain tensor components (distributions, time series), strain rate tensor components (distributions, time series) using the ultrasound echo signal obtained itself, a fundamental wave extracted (n=1) solo, one of harmonic waves extracted (n=2 to N) solo, or combinations of them.

The following is explanation of the beamforming (i.e., beam steering) and displacement measurement methods used in the drive/output controller or the data processing unit.

For this conduct form, the beam steering with a steering angle is performed as described in paragraphs 0035 to 0037 (FIG. 5a, two-dimensional case; 5b, three-dimensional case). As described in the paragraphs 0035 to 0037, the beam steering can be performed using the electric beamforming such as the apodization, switching, delay, phase matching, summation processing etc. Also as described in the paragraph 0033 (FIG. 2), the mechanical scan can also be performed by slanting the displacement/strain sensor. A synthetic aperture can also be performed.

For the case using the electric steering, when generating the steering beams, an arbitrary three-dimensional orthogonal coordinate system involving the existence of three axes of a depth direction, and the lateral and elevational directions or an arbitrary two-dimensional orthogonal coordinate system involving the existence of two axes of a depth direction and the lateral direction is formed. When the target tissue moves in a lateral direction dominantly, not a displacement vector measurement but a one-dimensional displacement measurement described specifically later is also applicable. In such a case, in order to increase the measurement accuracy, the coordinate system is set such that not an axial direction but a lateral direction corresponds to the direction of the target motion. In such a case, the mechanical scan may also be performed by slanting the displacement/strain sensor 5. When the target tissue dominantly moves in the depth direction, the one-dimensional displacement measurement should be performed under the condition that the beam direction corresponds to the depth direction. That is, either axial or lateral axis should be chosen such that easily the axis can be set in such a proper way. The beam steering should be performed such that the beam is steered in the direction of the target motion. Then, if necessary, the mechanical scan may also be performed by slanting the displacement/strain sensor 5. However, the one-dimensional displacement measurement should used for the measurement of a lateral displacement. A synthetic aperture may also be performed.

When performing the mechanical beam steering, the displacement/strain sensor 5 is slanted with respect to the object by the mechanical scanning (FIG. 6). In such a case, the mechanical steering angle θm shown in FIG. 6 is sensed, which is used for forming a three-dimensional orthogonal coordinate system involving the existence of three axes of a depth direction, and the lateral and elevational directions or a two-dimensional orthogonal coordinate system involving the existence of two axes of a depth direction and the lateral direction. Alternatively, after beamforming using a three- or two-dimensional orthogonal coordinate system without using the mechanical steering angle θm, the coordinate system is rotated using the mechanical steering angle θm such that the same coordinate system having an axis of a depth direction at least (FIG. 6). In such a case, the steered beam data digitized by A/D conversion are interpolated to obtain the data over the coordinate system reformed. Also in the case of mechanical scan, when the target tissue moves in a lateral direction dominantly, not a displacement vector measurement but a one-dimensional displacement measurement described specifically later is also applicable. In such a case, in order to increase the measurement accuracy, the coordinate system is set such that not an axial direction but a lateral direction corresponds to the direction of the target motion. When the target tissue dominantly moves in the depth direction, the one-dimensional displacement measurement should be performed under the condition that the beam direction corresponds to the depth direction. That is, either axial or lateral axis should be chosen such that easily the axis can be set in such a proper way. The beam steering should be performed such that the beam is steered in the direction of the target motion. A synthetic aperture may also be used together.

Strictly, the interpolation processing should be performed using the above-described phase matching on the basis of the Nyquist theorem (see ref. 1: The value at the desired position is obtained by spatially shifting the echo data by multiplying a complex exponential expressed using the spatial shift to be realized to the Fourier's transform of the echo data). However, the other interpolations such as the linear interpolation etc can also be performed as the approximate interpolations. For the measurement of spatial displacement distributions, the object is scanned using a steering beam with a single steering angle. For the scanning, the direction of the scanning should correspond to that of the lateral direction of the coordinate system to be used finally. It is absolutely required that every sampling point in the ROI has a steering angle not equal to zero at least (For the lateral modulation, crossed beams are required at each point). For instance, when using a convex- or sector-type transducer, a single steering angle should be realized with respect to the depth direction (axis) of the orthogonal coordinate system that is determined by the curvature of the aperture used. The object should be scanned in the lateral direction (axis) simultaneously set. A synthetic aperture can also be performed. Otherwise, as described above, a steering beam with a single steering angle is used over an arbitrary orthogonal coordinate system because an arbitrary shape beam can be tried to be steered in an arbitrary direction within a limitation regardless the aperture geometry by beamforming on the basis the delay, phase matching, summation and apodization or virtual source and receiver described later. Generally, the error of the steering angle with respect to the desired one leads to the measurement error, the displacement measurement methods used or of the present inventions are robust to such an error.

Figure 7:
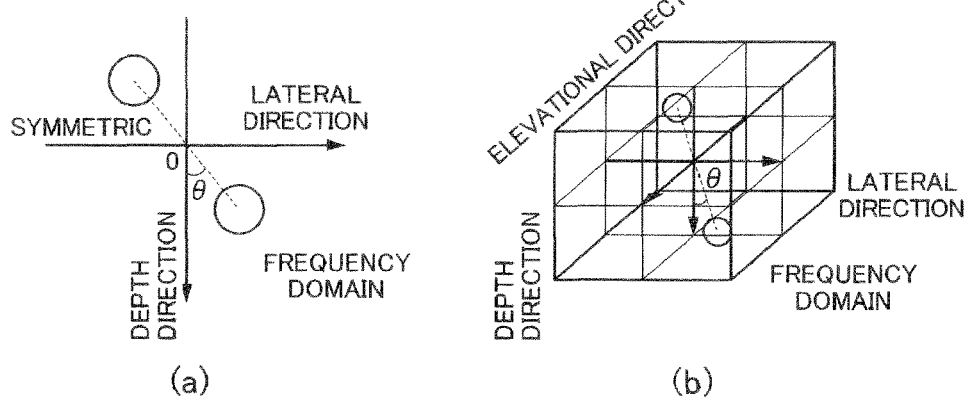
FIG. 7 shows (a) two-dimensional and (b) three-dimensional spectra for a lateral scan using steering beams with a single steering angle as show in FIG. 5.

As the results, for the respective two- and three-dimensional ROIs, a single quadrant (FIG. 7a) and a single octant (FIG. 7b) spectra are obtained. In both frequency domains, the same single spectra exist symmetrically with respect to the origin. The "θ" shown in FIG. 7 corresponds to the steering angle "θ" shown in FIG. 5.

Figure 8:
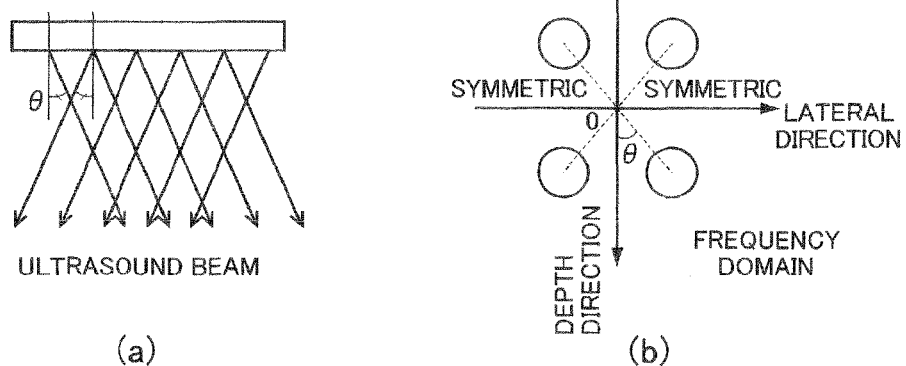
FIG. 8 shows for two-dimensional region of interest (ROI), illustrations of (a) crossed, steering beams for a lateral modulation and (b) the corresponding spectra.

The lateral modulation described in the paragraph 0013 can be obtained in a two-dimensional ROI case by generating the crossed beams in a laterally symmetric condition using the steered beams of the present invention as shown in FIG. 8a (ref. 3). Then, when the single spectra obtained by the single steering angle used in the present invent is illustrated in FIG. 7a, that of the lateral modulation is illustrated in FIG. 8b. That is, independent two single quadrant spectra are obtained. In the three-dimensional ROI case, the lateral modulation is equivalent to the crossed three or four steered beams. As the results, three or four octant spectra are obtained in a frequency domain (see FIG. 1a in ref. 3). According to the measurement accuracy required for the displacement vector measurement or one-directional displacement, the lateral modulation should also be selected by a switching. Then, the displacement measurement apparatus is also equipped with a function that allows the generation of the symmetric steered beams, i.e., crossed beams. In such a case, the echo imaging on the basis of the lateral modulation is also performed. Thus, in such a case, a high spatial resolution can be obtained for the echo imaging in both the axial and lateral directions. A synthetic aperture may also be performed.

For the lateral modulation, the point is that crossed beams must be realized. That is, for an arbitrary coordinate system realized by an arbitrary type transducer, crossed beams must be realized anyway. Non-symmetric crossed beams can also be used with respect to the axis of a depth direction, if obstacles such as bones exist in the superficial region. Plural transducers can also be used. The mechanical scan may also be performed together. At each position in the ROI, the steering angle or the angle between the crossed beams should be as large as possible. In order to control the measurement accuracies of the displacement vector components, as described above, the coordinate system can be controlled. The coordinate control is described specifically later. When using one-dimensional displacement measurement methods, the symmetric beams obtained by the coordinate rotation are demodulated as described specifically later.

When performing the lateral modulation, the multidimensional displacement vector can also be measured using the multidimensional displacement vector measurement methods such as the multidimensional cross-spectrum phase gradient method (MCSPGM, refs. 1 and 2), the multidimensional autocorrelation method (MAM, ref. 3) and the multidimensional Doppler method (MDM, ref. 3).

Figure 9:
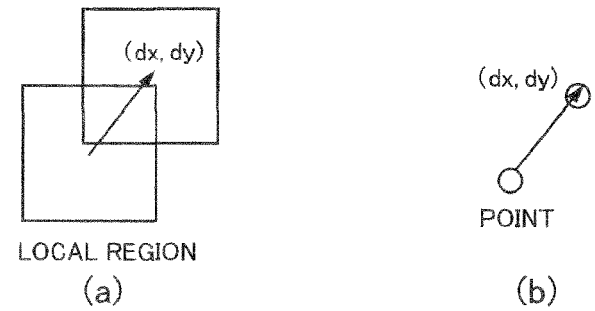
FIG. 9 shows illustrations of (a) a local rigid motion in a two-dimensional ROI and (b) a displacement of a point.

MCSPGM calculates the local displacement vector between the echo data frames obtained at two phases (different times) using the local phase characteristics under the assumption of a rigid motion. Then, the method falls in a category of the block matching method. Specifically, an analogue displacement vector measurement can be obtained in a frequency domain by applying the least squares method to the gradient of the local cross-spectrum phase obtained from the digitized two echo data frames. For instance, the measurement of local two displacement components in a two-dimensional ROI is illustrated in FIG. 9a. Similarly, the local three displacement vector components can also be measured for the three-dimensional ROI.

The cross-correlation method and Sum absolute difference (SAD) method are also block matching methods. These two methods are also used for the compression of dynamic image data etc. However, for the tissue displacement measurement, these two methods yield only displacement data expressed by the multiplications of the integers and the sampling intervals in the respective directions. Then, these two methods can be used not for the fine measurements but coarse measurements.

Alternatively, MAM and MDM calculates the two and three displacement vector components at each position in the ROI by solving the simultaneous equations derived from the two- or three-dimensional analytic signals obtained from the respective independent single quadrant and octant spectra (paragraph 0068) at two phases (different times). For instance, the measurement of two displacement components at a position in a two-dimensional ROI is illustrated in FIG. 9b. Similarly, the three displacement vector components at a position can also be measured for the three-dimensional ROI. In the case dealing with a three-dimensional displacement vector components, four or three independent octant spectra are used, whereas in the case dealing with a two-dimensional displacement vector components, two independent quadrant spectra are used. Then, occasionally, the least squares method can be used to solve the simultaneous equations.

In the derived equations at each position, the coefficients multiplied to the unknown displacement vector components are instantaneous frequencies of the echo signal at the position, whereas the constants are the difference of the instantaneous phases obtained at two phases (different times). To stabilize the displacement vector measurements, the instantaneous frequencies and the difference of the instantaneous phases are calculated with a moving-average. Alternatively, in another version of the MAM and MDM, the assumption of the rigid motion can also be used similarly to the MCSPGM. That is, one displacement vector is dealt with for a local region. Then, the least squares method is used to solve the simultaneous equations derived for the local region in which number of the position is larger than the number of unknown displacement components. Because the MAM and MDM solved in the manner also falls in a category of a block matching method similarly to the MCSPGM, the MAM and MDM are referred to as MAMb and MDMb. Also for the MAMb and MDMb, the same moving-average may also be performed to calculate the instantaneous frequencies and the difference of the instantaneous phases.

The MAMb and MDMb without the calculations using moving-average but the least squares method solo require fewer calculations. In general, however, a block matching method yields less accuracy in the measurements of the strains and their spatial distributions as well as the rigid motion as we clarified. The spatial resolution of the displacement vector measurement is determined by the width of the moving-average or the local region size used.

Alternatively, the corresponding one-dimensional or one-directional displacement measurement methods such as one-dimensional Doppler method have the almost 50-years history in the no lateral modulation case. As described above, the beam is tried to be steered in the direction of the target motion such that the carrier frequency in the direction of the target motion is realized. Correspondingly, we have also the one-dimensional cross-spectrum phase gradient method, autocorrelation method, cross-correlation method and SAD.

However, for instance, there is a limitation about the measurement accuracy achieved although the beam is tried to be steered in the direction of the blood flow if the blood vessel runs parallel to the body surface (FIG. 6). It is also difficult to measure the liver motion that moves and deforms in the lateral direction with a relation to a hear motion. There is also limitation about the accuracy of the measurement of the complex motion and deformation such as the hear motion and blood flow in the heart. In such cases, i.e., the target also moves in the lateral or elevational direction, the combination of the lateral modulation and multidimensional displacement vector measurement methods is effective. The combination allows the increase in the measurement accuracy of the displacement in the depth direction as well as the lateral displacement measurement. The combination also achieves the simple manual measurement, i.e., the transducer is only attached onto the target surface in the neighborhood of the target region.

For the measurements of elasticity and strain of breast and thyroid, the transducer can be used as a compressor. Then, in such cases, the one-directional displacement measurement methods can also be used. However, if the target tissue moves out of the beams transmitted, the measurement accuracy degrades. Then, as described in paragraphs 0010 to 0011, the multidimensional phase matching method the present inventor invented previously must also be used together.

Thus, the multidimensional phase matching method also increases the measurement accuracy of the displacement vector. The multidimensional phase matching can also be used when the lateral modulation is performed. Although in such a case, the demodulation methods described in refs. 9 and 10 can be used, the demodulation method of the present invention described later that realizes more accurate demodulation can also be used. If the crossed beams and the corresponding spectra obtained are not symmetric with respect to the axial direction, the demodulation is performed after the rotation of the coordinate system.

The demodulation methods generate the phases that are expressed using the respective displacement components, from which the respective displacement components are calculated. In the demodulation of the present invention, when the two-dimensional displacement vector (dx, dy) is measured, the difference in the instantaneous phase at a position in the two-dimensional ROI obtained from the two echo data frames obtained at the two phases (time differences) are expressed using the phases of the analytic signals expj(fxdx+fydy) and expj(fxdx-fydy) obtained from the independent single quadrant spectra shown in FIG. 8b. By calculating the product and conjugate product of the analytic signals, the complex signals expj(2fxdx) and expj(2fydy) are obtained. Then the respective displacement vector components dx and dy can be calculated by dividing the phases of the complex signals by the respective twofold instantaneous frequencies 2fx and 2fy. Because the product and the conjugate product yield twofold frequency in the respective directions, the beamforming must be performed with a lateral bandwidth large enough in advance. Otherwise, the interpolations of beams may be performed in a spatial domain or in a frequency domain, i.e., zero padding in a frequency domain.

The demodulation can also be performed for the measurement of the three-dimensional displacement vector measurement (dx, dy, dz). At least the three analytic signals among the four signals expj(fxdx+fydy+fzdz), expj(fxdx+fydy-fzdz), expj(fxdx-fydy+fzdz) and expj(fxdx-fydy-fzdz) (see FIG. 1a shown in ref. 3) are used. Also in this case, the product and the conjugate product yield twofold instantaneous frequencies in the respective directions. Then, in the same manner, the beamforming must be performed with a lateral bandwidth large enough in advance. Otherwise, the interpolations of beams may be performed in a spatial domain or in a frequency domain, i.e., zero padding in a frequency domain.

However, even if the multidimensional phase matching is performed, the residual displacement remained leads to the measurement error. Then, the measurement obtained using the one-dimensional displacement measurement methods yield lower accuracy than that obtained by using the corresponding multidimensional displacement vector measurement methods. The larger the residual displacements, the larger measurement errors are yielded. That is, the measurement errors inherent to the one-dimensional displacement measurement methods occur.

Next, the multidimensional cross-spectrum phase gradient method (MCSPGM), the multidimensional autocorrelation method with a block matching (MAMb) and the multidimensional Doppler method with a block matching (MDMb) among the multidimensional displacement vector measurement methods that can be used for the lateral modulation can also be used for the beam steering with a single steering angle. A synthetic aperture can also be performed. All the methods fall in a category of a block matching type. In conjunction, the multidimensional cross-correlation method and SAD can also be used similarly. The beam steering increases the measurement accuracy of the displacement vector because the lateral carrier frequency can also be obtained. However, as mentioned above, the lateral modulation should be performed to yield more accurate measurements, because these block matching types will not yield the high accuracy for the single beam steering angle.

For the single steering angle case, the measurements of three- or two-dimensional displacement vector, or one-directional displacement can also be performed by dividing the single quadrant or octant spectra, or one-dimensional spectra to yield plural analytic signals. That is, the analytic signals obtained from the respective same bandwidths divided for the two echo data frames are used to derive the simultaneous equations about the unknown displacements at each position in the ROI. For the frequency division, a kind of window can also be used. Non-divided spectra can also be used together. In these cases, in addition to the block matching types, MCSPGM, MAM, MDM and the corresponding one-dimensional methods can also be used. The spectra around of the ultrasound frequency and lateral frequency can be used mainly. High or low frequency spectra can be used mainly. The spectra with a high SNR can also be used mainly. In conjunction, the weighted simultaneous equations can be obtained by considering the accuracy or confidence of the corresponding spectra used (not used spectra correspond to the condition that the weighted assigned is zero). The number of equations derived should be larger than that of unknown displacement components. The frequency division can also be implemented on the lateral modulation. The least squares method and the regularization are implemented for solving the equations.

Figure 10:
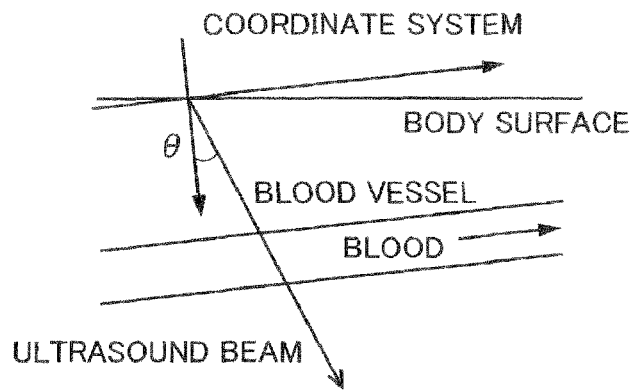
FIG. 10 shows an illustration for measuring blood flow in a blood vessel running parallel to the body surface using electrically or mechanically steered beams under the condition of setting a lateral axis of a coordinate system such that the lateral axis corresponds to the direction of the target displacement.

For the single steering angle, the following displacement measurement methods can be used for the measurement of the one-directional displacement such as a lateral or elevational displacement. A synthetic aperture may also be performed. Although the displacement of the depth direction can also be measured using the one-directional displacement measurement method, the measurements of the dominant lateral and elevational displacements are performed when using the method. For the lateral displacement measurement, if the target displacement exits in the remaining two orthogonal axes, measurement errors occur as described later. Then, with seeing a blood flow image (displacement or velocity), a tissue displacement image or a tissue strain image obtained using the B-mode image, the methods of the present inventions (may still have low accuracy at the moment) or other methods or modalities, not the beam direction but the lateral direction is set in the direction of the target motion (FIG. 10). In FIG. 10, A expresses the steering angle confirmed in the coordinate system finally defined. Also in this case, the above-described frequency division can be performed.

As described above, also the mechanical steering angle θm (FIG. 6) is detected by a proper sensor. If necessary, by using a display and a pen as interfaces, the angle to be corrected is detected. In order to set the coordinate system properly at performing the beamforming or after performing the beamforming, the electric beam steering angle value (FIG. 5) and the mechanical steering angle value to be corrected (FIG. 6) may be indicated or displayed. The angles detected may be indicated or displayed in the polar coordinate system to visually confirm if the angles are proper. The indicated or displayed angles may be used to automatically form the proper coordinate system and the proper steered beams through the electric beam steering or the mechanical beam steering. A synthetic aperture may also be performed or using the same echo data set stored. The evaluation of the angles to be corrected may also be automatically performed by detecting the tissue structures such as a vessel wall in the ultrasound images or measuring the direction of the displacement etc. The measured displacement distribution data can also be used. The frequency division method can also be used. Although the automatic correction is desirable, the manual correction may also be performed using the proper device such as the sensor.

Thus, for the one-directional displacement measurement achieved by using the following displacement measurement methods, the finally achieved proper coordinate system can be obtained by choosing an axis that is the most easily set in the direction of the target motion regardless the coordinate system is three-, two- or one-dimensional. Then, if the target tissue moves in the lateral direction dominantly, not the depth axis but the lateral axis is set in the motion direction. Such a lateral one-dimensional displacement measurement does not lead to the measurement errors caused when using the conventional axial one-dimensional displacement measurement used under the condition that the beam direction cannot set in the direction of the target motion. Similarly to the lateral modulation, the configurations of the displacement/strain sensor and the object become simple and the measurement accuracy achieved also becomes high.

Figure 11:
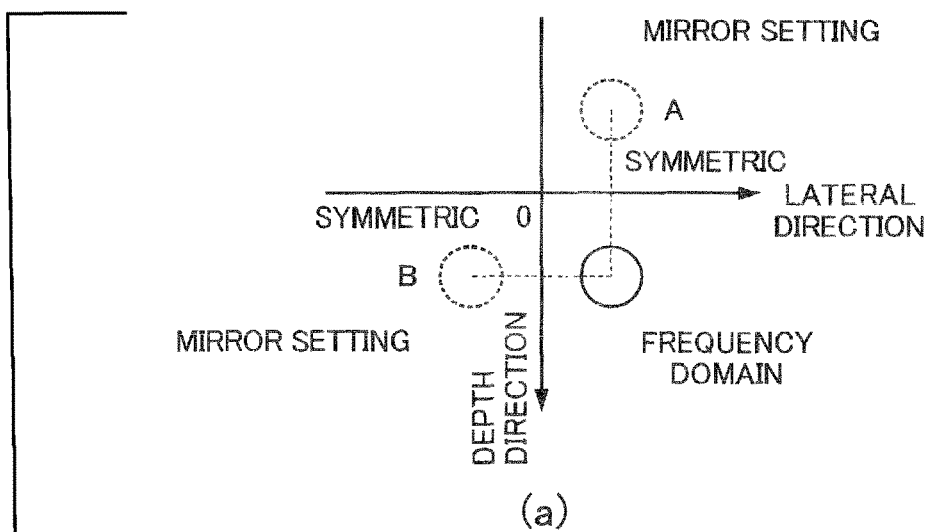
FIG. 11 shows illustrations for a two-dimensional case, (a) mirror setting in a frequency domain, and mirror setting in a spatial domain for (b) axial and (c) lateral directions.
Figure 11:
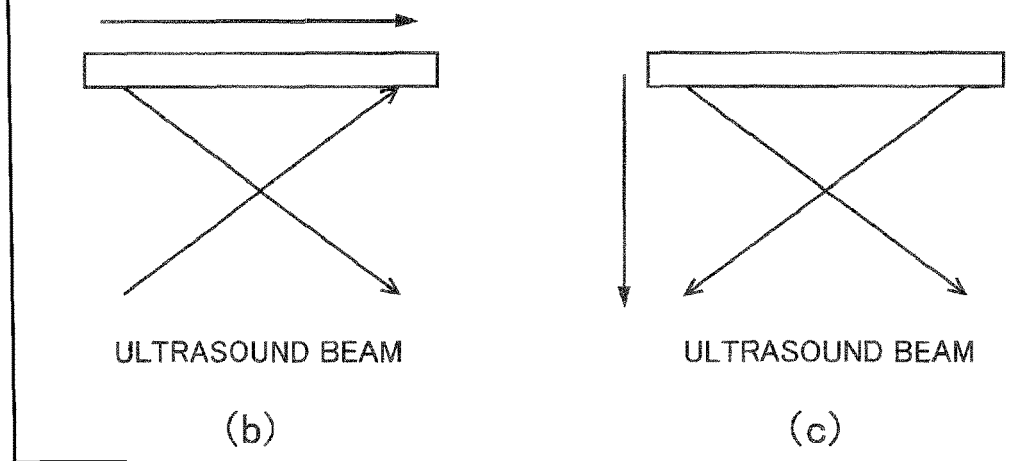

Although the block matching method can also be used for such a measurement, it is also possible to measure the one-directional displacement (distribution, time series) by implementing the MAM or MDM on the mirror-set echo data frames obtained at two phases (different times). The mirror setting can also be performed in a frequency domain. For instance, in the two-dimensional case, the setting the single quadrant spectra at the position A or B in a mirror condition as shown in FIG. 11a realizes the mirror setting of the echo data in the axial direction with respect to the lateral axis (FIG. 11b) or in the lateral direction with respect to the axial axis (FIG. 11c). Otherwise, in a spatial domain, the mirror setting can also be performed as shown in FIGS. 11b and 11c. Basically, the mirror setting is performed locally. By superimposing the mirror-set spectra and beams on the original spectra and beams, the quasi-lateral modulation imaging can also be performed. The mirror setting can also be used for the three-dimensional case. The mirror setting can also be used for the displacement measurements.

With the mirror setting of steered echo data, more than the number of independent single quadrant (two-dimensional case) or octant (three-dimensional case) spectra required by MAM and MDM are obtained, by which independent equations more than the number of unknown displacements can be obtained. The mirror settings shown in FIGS. 11b and 11c realized in a spatial or frequency domain are respectively used for the measurements of the dominant lateral and axial displacements. Because the tissue motion in the depth direction can be measured with a high accuracy by using conventional one-dimensional displacement measurement methods, the mirror setting shown in FIG. 11b is effective, particularly for the measurement of the dominant lateral displacement. Also in this case, the above described frequency division method can be used, if necessary.

Hereafter, as the one-directional displacement measurement, the dominant lateral displacement is dealt with mainly. Under the condition that the lateral axis is set in the direction of the target lateral motion (FIG. 10), the mirror setting allows the measurement of the lateral displacement as a one-directional displacement measurement. However, only if a displacement in the axial or elevational direction exists, the measurement errors occur. For instance, at a position in the two-dimensional region, the equation about the unknown two-dimensional displacement vector (dx,dy) is obtained from the original single quadrant spectra, i.e., $$fxdx+fydy=c \quad (1)$$

and the mirror setting derives the following equation, i.e., $$-fxdx'+fydy=c$$

$$\text{where } dx'=-dx \quad (1)'$$

Moreover, c expresses the difference of the instantaneous phase between the two echo signal at the position; and fx and fy are the instantaneous frequencies in the respective directions at the position. If the axial displacement dx equals to zero, the equations (1) and (1)' simultaneously solved yields dx=0 and dy=c/fy under the condition that dx'=dx. However, if dx≠0, (1)' solved by dealing with (dx', dy) as (dx, dy) leads to measurement errors. This is also for the three-dimensional case. Thus, one can confirm that the proper setting of the coordinate system is important.

The one-directional displacement measurement has an effect on the measurement of the dominant lateral displacement. Then, it is needless to say that the one-directional displacement measurement method is a lateral one-directional displacement measurement method. In order to obtain the measurement accuracy, the coordinate system to be final used has a lateral axis of which direction corresponds to that of the lateral motion (FIG. 10), i.e., not axial axis. For instance, for the measurement of the blood flow in thyroid as shown in FIG. 6, the lateral one-dimensional displacement measurement does not lead to the measurement errors caused when using the conventional axial one-dimensional displacement measurement used under the condition that the beam direction cannot set in the direction of the target motion. Similarly to the lateral modulation (LM), the configurations of the displacement/strain sensor and the object become simple and the measurement accuracy achieved also becomes high.

For the lateral one-directional displacement measurement, the displacement can also be measured using other above-described one-directional displacement measurement methods such as the one-dimensional cross-spectrum phase gradient method, one-dimensional autocorrelation method, one-dimensional Doppler method, one-dimensional cross-correlation method, one-dimensional SAD from the MAM and MDM. When using these methods, being different from the uses of the MAM and MDM, the mirror setting is not required. Also being different from the lateral modulation, the demodulation described above is not required. With these methods, the lateral displacement can be measured as c/fy. That is, the lateral displacement can be calculated by dividing the difference of the instantaneous phase by the instantaneous lateral frequency. Also an dominant axial displacement can also be measured similarly. Also in these cases, the frequency division method described above can be used.

However, note that the phase matching, moving-average and block matching should be performed in the two- or three-dimensional region, by which the measurement accuracy becomes higher than the measurement using only the echo data on the respective one-dimensional regions (i.e., lateral ones). However, these measurements cannot achieve the accuracy obtained by the mirror setting and the corresponding multidimensional displacement vector measurement methods etc.

The measurement error for the lateral displacement measurement generated by the one-directional displacement measurement due to the displacement of the depth direction dx≠0 is expressed by -(fx/fy)×dx. Similarly to the case using the MAM and MDM with the mirror setting, in order to obtain the high accuracy of the lateral displacement measurement, the lateral axis of the coordinate system, should be set in the direction of the lateral motion. However, when dx≠0, if the single quadrant spectra with a minus axial frequency correspondingly obtained from the beam steered in the direction of the target motion, the displacement weighted with the instantaneous frequencies [(fx/fy)×dx+dy] is obtained as the measurement result. If the steering angle shown in FIGS. 5a, 6 and 10 is set to 45°, the summation of the displacement components [dx+dy] is calculated because fx=fy. Such calculations are also performed for the three-dimensional displacement vector measurement. If dx≠0 and dz≠0, (fx/fy)×dx+(fz/fy)×dz+dy is calculated as the measurement result. When setting the steering angle to 45°, the summation of the displacement components dx+dy+dz is calculated. Also in this case, the above frequency division can also be performed.

Regarding the multidimensional displacement vector measurement methods and the one-directional displacement measurement methods above-mentioned or described, the measurement accuracy can be compared. Regarding the displacement vector measurement, the order of the measurement accuracy evaluated by the present inventor is (LM+MAM, MDM)>(LM+MAMb, MDMb, MCSPGM)>(a single steering angle+MAMb, MDMb, MCSPGM). That is, the type of a block matching yields a low measurement accuracy; the LM (lateral modulation) yields a higher measurement accuracy than the single beam steering angle. Although the combination of the demodulation method of the present invention and the one-directional displacement measurement methods also allows the displacement vector measurement, the measurement accuracy achieved is lower than the obtained by the corresponding multidimensional displacement vector measurement methods. For the LM and the beam steering with a single steering angle, a synthetic aperture can also be used.

For the lateral or one-directional displacement measurement, the order of the measurement accuracy is (a single steering angle+mirror setting+MAM, MDM)>(LM+MAM, MDM) or (a single steering angle+one-directional displacement measurement method)>(LM+one-directional displacement measurement method). Interestingly, for the measurement of the one-directional displacement, the beam steering with a single steering angle yields a higher measurement accuracy than the LM. The one-directional displacement measurement method yields a lower measurement accuracy than the corresponding multidimensional displacement vector measurement methods. Also the type of a block matching yields a low measurement accuracy. For the LM and the beam steering with a single steering angle, a synthetic aperture can also be used.

Next, the quality of the beamforming is compared for the lateral modulation and the beam steering with a single steering angle. With LM, the following properties may lead to the deterioration of measurement accuracy:
(1) When a synthetic aperture is used for yielding plural steered beams, the ultrasound intensity transmitted from an element is small, which may yield low SNR echo data.
(2) Alternatively, when crossed beams are superimposed, although a large ultrasound intensity can be obtained, time differences between the transmission of the beams can cause measurement errors, if the displacement occurs during these time differences.
(3) Because multiple beams that have different paths are used, the inhomogeneity of tissue properties affects beamforming. Specifically, propagation speed affects focusing (i.e., the beam-crossing position), whereas attenuation and scattering lead to different frequencies of the crossed beams.
(4) At the minimum, more time is required to complete a beamforming than that required with ASTA. Occasionally, more time is also required to complete a displacement calculation than is required with ASTA.

In contrast, with the beam steering with a single steering angle, the number of available displacement vector measurement methods is limited. Being dependent on the measurement method, only a lateral displacement measurement can be performed, and any of the above concerns, points 1 to 4, will not become a problem, and a simple beam forming increases the ability to make real-time measurements together with higher accuracy in displacement measurements. However, if the ultrasound intensity transmitted from an ultrasound element is large enough, the tissue displacement during the echo data acquisition or the inhomogeneity of the tissue ultrasound properties does not become a problem, the lateral modulation using the plural beams yields a higher echo SNR owing to the large number of the summation of echo signals at performing the beamforming.

However, with LM, point (1) can be managed with new virtual sources of the present inventions described below. Moreover, new virtual sources of the present inventions described below also cope with another LM problem: a deeply situated tissue cannot be dealt with, because a larger physical aperture is required than that for a conventional beamforming; the vision of field (VOF) becomes narrower in the lateral and elevational directions; these problems become more sever if obstacles such as a bone exist in a superficial region.

Figure 12:
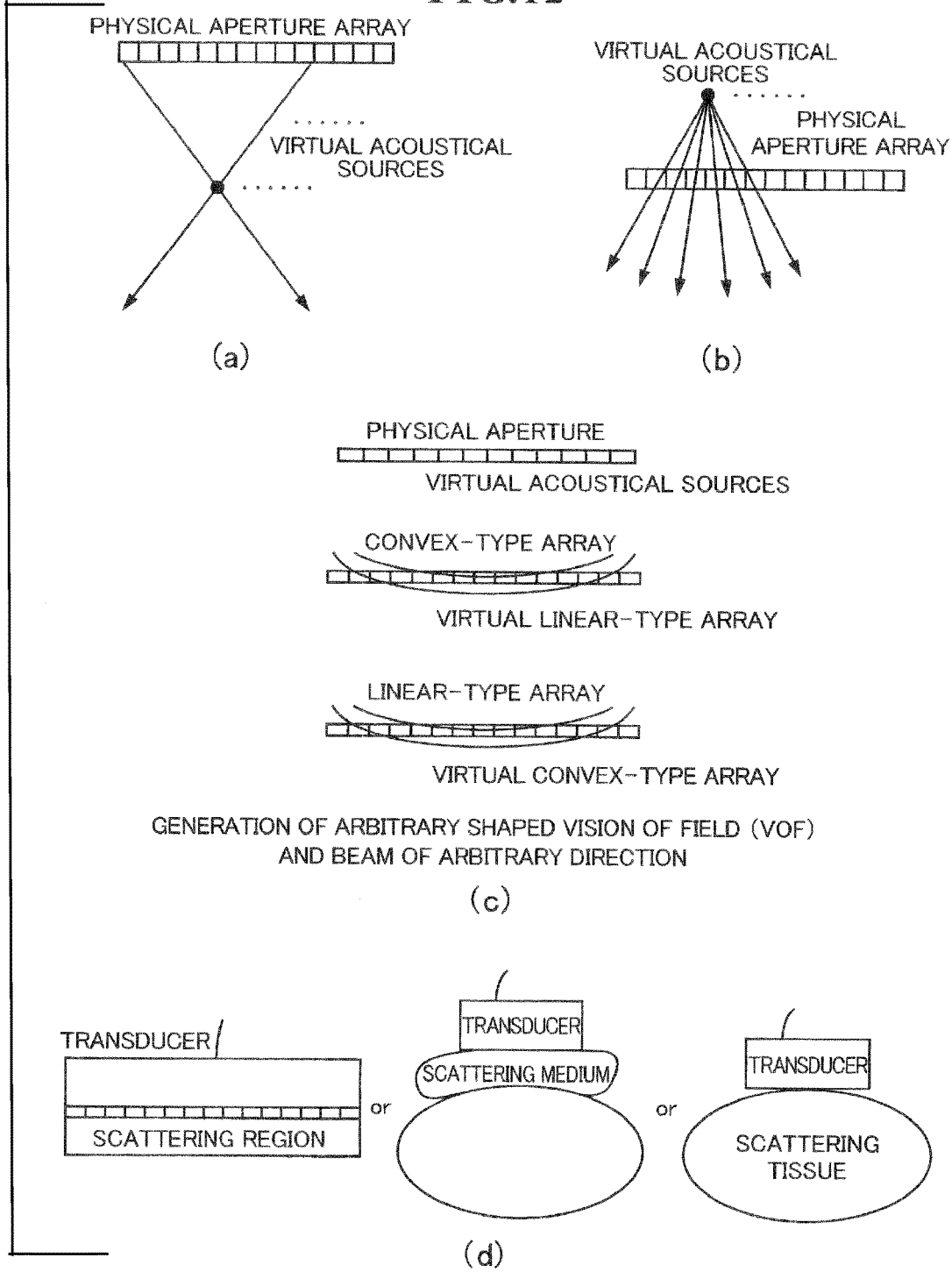
FIG. 12 shows illustrations for virtual sources as follows, (a) a known virtual source that is realized at a focus position of beamforming using a physical aperture or array elements, (b) a known virtual source that gains a transmission power and a virtual receiver, and (c) and (d) virtual sources that are realized regardless the position of a focus of beamforming using a physical aperture or array elements, specifically, (c) a virtual source for regenerations of an arbitrary vision of field (VOF) and an arbitrary beam direction and (d) a virtual source realized by scatters.

A previously reported virtual source can increase the lateral spatial resolution of a B-mode image (ref. 11: C. H. Frazier et al, IEEE Trans. UFFC, vol. 45, pp. 196-207, 1998). As shown in FIG. 12a, the virtual source is set at the focus position of an ultrasound physical aperture, an array element or a beamforming, of which lateral resolution is also realized in the respective depths. Since the virtual sources are set in front of the physical aperture(s), the transmission intensity form a virtual source becomes larger than that from an array element. However, the echo imaging and the displacement measurement cannot be performed around the virtual sources and in the superficial regions in the neighborhood of the transducer.

The measurement controller 3 in the apparatus shown in FIG. 1 can set virtual sources behind the physical array elements to increase the transmission intensity of ultrasound (FIG. 12b). That is, it becomes possible to transmit the ultrasounds from plural elements with respect to a virtual source set. The virtual source also allows the echo imaging and the displacement measurement in the superficial tissues.

The measurement controller 3 in the apparatus of the present invention (FIG. 1) can also set virtual receives and virtual sources as shown in respective FIGS. 12c and 12d regardless the focus position of the physical aperture, array elements and the beamforming. Then, a synthetic aperture can be performed with respect to the virtual sources and receivers by finding echo signals generated by the scattering or reflection at the point of interest. The virtual sources of the present inventions allow the extending of the VOF in all the directions. Moreover, the virtual sources of the present inventions yield an arbitrary shaped beam in an arbitrary direction regardless the geometry of the transducer aperture (FIG. 12c). Moreover, the virtual sources of the present inventions can also be realized by using scatters or diffractions set in the neighborhood of the physical acoustical sources, for instance, by putting the material including the scattered or diffractions (FIG. 12d). Small holes can also be used. That is, these are dealt with as acoustical sources. The scatters in the target object (tissues etc) can also be used as the virtual sources.

Thus, the positions of the virtual sources of the present inventions are set strictly or not (however, proper concentrations, sizes and geometries of the scattering are required). The virtual sources of the present invention allow the overcoming of the limitation about the lateral resolution determined by the physical aperture size (those of array elements etc). In the framework for desiring a point acoustical source, there exist tradeoffs among the region size of the acoustical spreading, the penetration and the SNR. The tradeoffs required the optimization of them. However, one should note that an intense ultrasound can be transmitted. A synthetic aperture can also be used. The controls of the impedance, geometry, size, position, structure, diffraction are required. Proper micro-bubbles can also be used.

For the synthetic aperture using the virtual sources, if necessary, the effect of the attenuation of propagating sound is corrected using a weight, e.g., determined by the distance between the physical aperture and the virtual source. Regarding the weighting, a spherical wave may be assumed to be transmitted from a point acoustical source. Some finite size aperture may also be assumed and analyzed analytically or numerically. Otherwise, for realizing a desired point spread function (PSF), the optimization method the present inventor previously invented can be used to determine the above-mentioned beamforming parameters such as the aperture size and geometry, transmission intensity (apodization) etc for the physical and virtual sources. There is also a case where many small aperture (size) is used although the transmission intensity from an aperture becomes small. The virtual sources and receivers of the present invention is effective for the lateral modulation, particularly. However, the effectiveness can also be obtained on the applications for the conventional beamformings and the beam steering with a single steering angle of the present invention. That is, the virtual sources can also be used for a real-time beamforming on the basis of the delay, phase matching and summation as well as a synthetic aperture.

In practical applications, a proper beamforming method should be selected for every organ and tissue (i.e., conventional beamformings, lateral modulation, beam steering with the single steering angle achieved by a real-time or a synthetic aperture), because every tissue has its own motion (heart, liver etc) and may also have obstacles such as bones (an effective aperture size to be used may be limited). Then, the echo SNR to be achieved depends on the target and the beamforming methods used. Being dependent on the echo SNR, the measurement accuracy including the spatial resolution achieved differs by the displacement measurement methods used (e.g., autocorrelation method, Doppler method, cross-spectrum phase gradient method etc). When the echo SNR is high, the order of the measurement accuracy is the autocorrelation method>cross-spectrum phase gradient method>Doppler method; and for the respective method, the multidimensional displacement vector measurement>one-dimensional displacement measurement. When the echo SNR is low, the orders are inverted. The calculation speeds obtained by the measurement methods also differ. These are specifically reported in ref. 3 by the present inventor. Thus, the beamforming methods, the displacement measurement methods or the combinations may be selected using the apparatus of the present invention. Because the suitable beamforming methods, displacement measurement methods or the combinations can be determined for every organ and tissue, they may be automatically selected by the apparatus of the present invention. The frequency division method may also be used.

Thus, the present invention supplies a new displacement measurement apparatus and a new ultrasound diagnosis apparatus having a remarkable feature that allows the selection of the proper beamforming (e.g., conventional beamformings, lateral modulation, beam steering with a single steering angle and others), the proper displacement measurement method or the proper combination. That is, the measurement controller and the data processing unit 1 used in the apparatuses possesses the function and/or method for selecting them (e.g., a manual or automatic selection).

As described above, in order to obtain a high measurement accuracy for the lateral displacement, the beam steering angle obtained by the electric and mechanical steering (θ in FIGS. 5, 6 and 10) is made as large as possible. A synthetic aperture may also be performed. The lateral carrier frequency is made as large as possible for the echo imaging and the lateral displacement measurement. The use of an extra large electric steering angle leads to a low echo SNR. Then, if necessary, the mechanical steering may also be used together with the electric steering.

The lateral carrier frequency is tried to made as large as possible. Accordingly, on the basis of the Nyquist theorem, the beam pitch is made small. That is, the generation of the aliasing (FIG. 13a) must be removed. This is also for the lateral modulation case.

Figure 13:
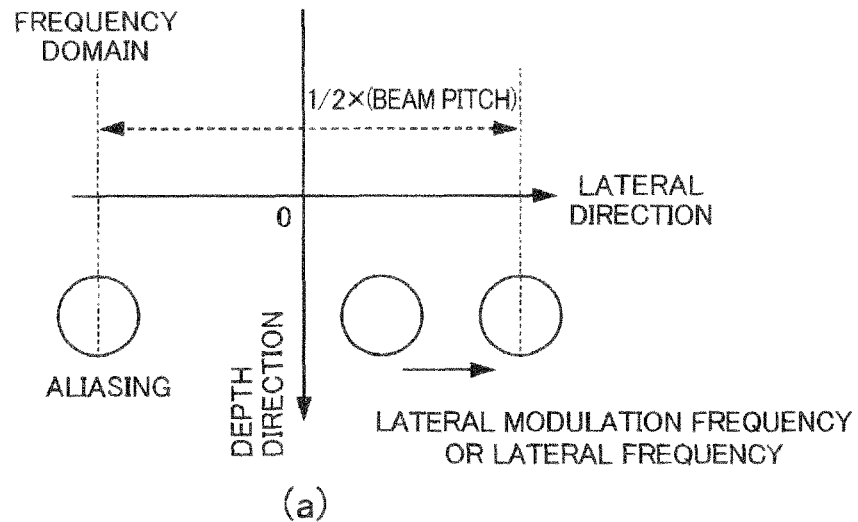
FIG. 13 shows illustrations for explaining (a) an aliasing generated when a steering angle is made large to increase a lateral carrier frequency under the condition that a beam pitch is coarse, (b) filtering in a frequency domain of the side lobes and grating lobes that grow when making the steering angle large, and (c) method for obtaining a higher lateral carrier frequency than the Nyquist frequency by making the steering angle large, i.e., widening a lateral bandwidth by padding zero spectra in higher frequencies than the Nyquist frequency (interpolations of lateral sampling points of a coordinate system)
Figure 13:
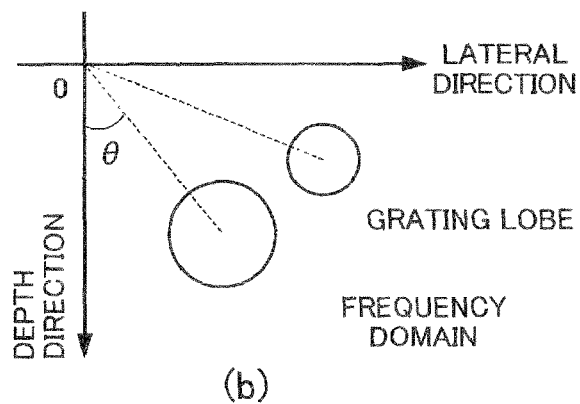
Figure 13:
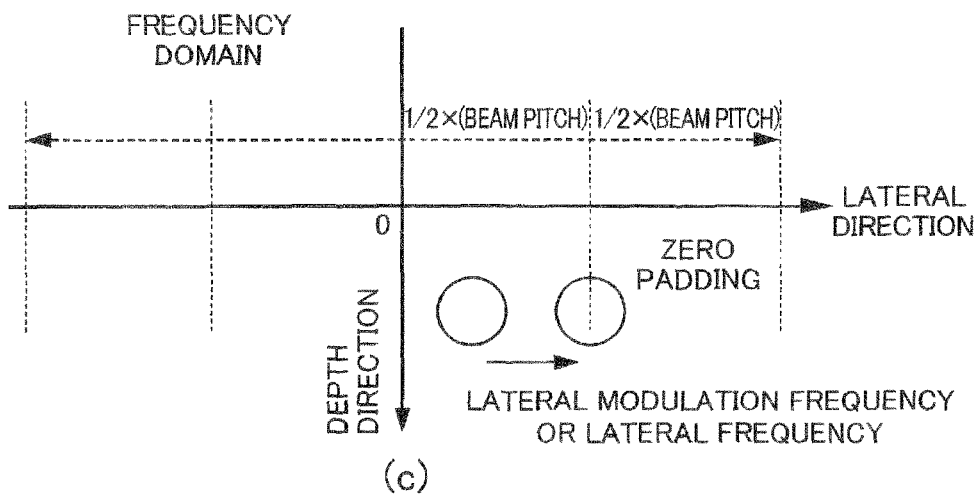

The use of the large steering angle may lead to the generations of the side lobes and grating lobes. Then, in the frequency domain, such lobes are filtered out by changing the corresponding spectra by zeros (FIG. 13b). Alternatively, by extracting the spectra, the corresponding steering beams can be separated. Then, the signal separation can also be performed with respect to the plural signals respectively arrived from different directions.

When it is possible to generate a large beam steering angle such that the higher lateral carrier frequency can be obtained than the highest frequency determined by the Nyquist theorem, the widening of the lateral bandwidth can be performed by padding zeros in the frequencies outside the original lateral bandwidth, i.e., the interpolations of the lateral sampling shown in FIG. 13c. The interpolations an also be performed in a spatial domain. Otherwise, the beamforming can also be performed with a small beam pitch. When realizing plural crossed beams for the lateral modulation, the widening of a lateral bandwidth is also effective. A synthetic aperture may also be performed.

Figure 14:
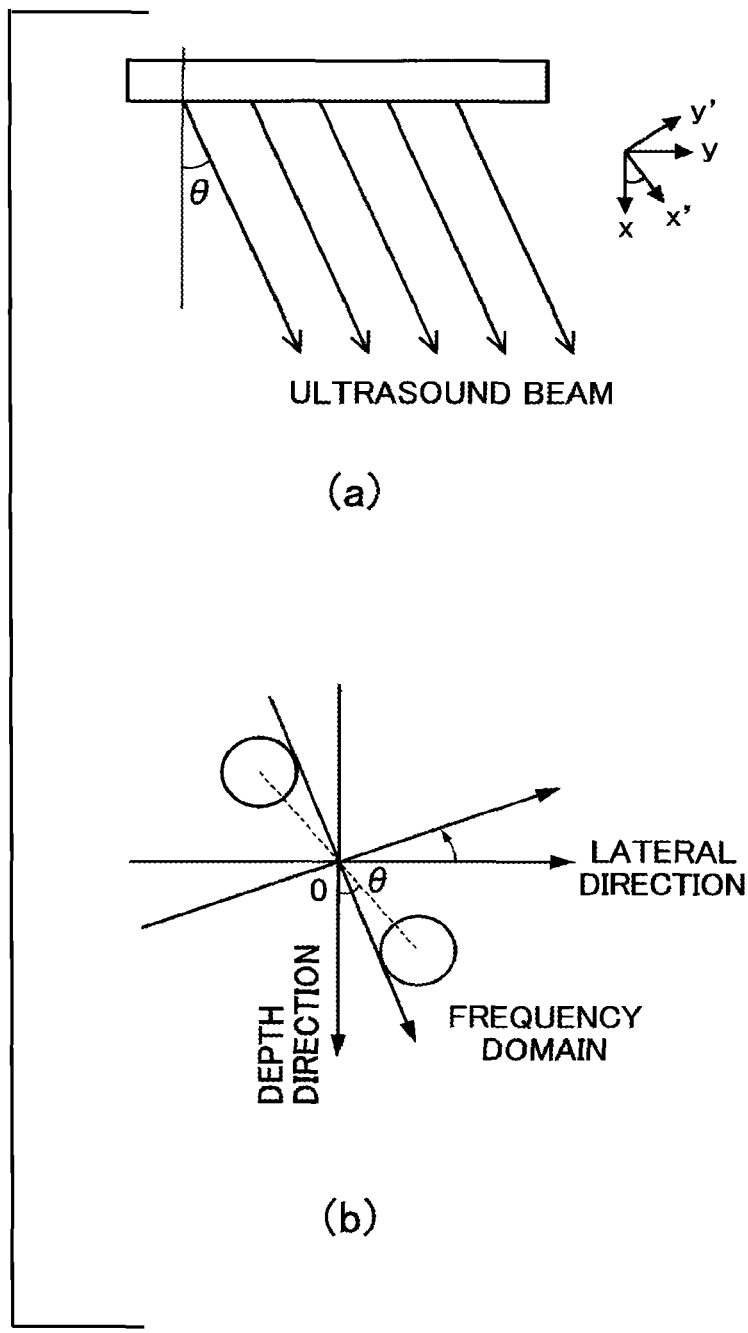
FIG. 14 shows illustrations for explaining a rotation of a coordinate system for an echo data frame obtained or to be obtained, i.e., a rotation after beamforming or at beamforming, and (b) the rotation of the coordinate system in a frequency domain.

When the electric steering solo cannot yield a high lateral or elevational carrier frequency, the application of the mechanical scan, the coordinate system of the echo data frames can be rotated (FIG. 14a). In order to control the measurement accuracies of displacement vector components, the rotation can also be performed. The rotation can also be performed in a frequency domain (FIG. 14b). However, for the measurement of a dominant lateral displacement, for instance, the blood flow in the vessel running parallel to the body surface, the beam must be tried to be steered in the direction of the displacement. A synthetic aperture may also be performed.

For the purposes, a fundamental wave, or harmonic waves of which higher axial carrier frequency and larger lateral bandwidth (narrower beam) respectively increase the measurement accuracy of the axial and lateral displacements, or all waves of which total single-to-noise ratio may be larger than that of the harmonic wave solo are properly used. That is, the echo imaging is performed using an ultrasound echo signal itself, a fundamental wave extracted (n=1) solo, one of harmonic waves extracted (n=2 to N) solo, or combinations of them. Moreover, the measurement of a displacement vector or a one-directional displacement (mainly, lateral one) is performed.

In the calculations, the displacement components may be obtained by simultaneously solving the equations derived from the respective echoes. In such cases, the equations may be weighted according to the confidence or SNR of the corresponding echoes (the least squares method or regularization may also be used). For the echo imaging, the respective signals corresponding to the spectra divided in a frequency domain may also be used, or the respective signals are superimposed after implementing such a weighting (signal non-used equals to the assignment of zero to the weight). Non-divided signal may also be used together. The superimposition may be performed after implementing a detection on the respective divided signals. Otherwise, after the superimposition of raw rf echo signals, a detection may be implemented on the superimposed signals. These are also for the lateral modulation or the non-steering case.

In these case, the data processing unit 1 may also calculate the strain tensor components (distributions, time series) by implementing a 3D, 2D or 1D spatial differential filter with a cutoff frequency in a spatial domain or their frequency responses to the measured three- or two-dimensional displacement vector components (distributions, time series) in the three-dimensional ROI, two-dimensional displacement vector components (distributions, time series) in the two-dimensional ROI, one-directional displacement (distribution, time series) in the three-, two- or one-dimensional ROI. The data processing unit 1 may also calculate the strain rate tensor components (distributions, time series), acceleration vector components (distributions, time series) and velocity vector components (distributions, time series) by implementing the temporal differential filter with a cutoff frequency or the frequency response to the measured time series of displacements or strains.

The measurement results can be displayed by the display unit 10 (FIG. 1) such as CRT etc, i.e., at least one of measured displacement vector components or displacement, strain tensor components or strain, strain rate tensor components or strain rate, acceleration vector components or acceleration, velocity vector components or velocity, the distribution, the time series and the corresponding B-mode image obtained by implementing the envelope or square detection etc. For the tensors, the principal strain and strain rate may be respectively calculated and displayed similarly. If necessary, similar to the color Doppler, power Doppler, Elastography etc, the measured distribution may be displayed using colors in the B-mode image. Other display scheme can also be used if the spatial resolution is yielded for the spatial position, the direction, magnitude (intensity) etc. The vectors, principal strains and principal strain rates may also be displayed using a vector line map. These may be superimposed each other for the purpose of the exhibition.

Thus, the present invention supplies new methods and apparatuses (techniques) on the basis of the scanning using the steering beam with a single steering angle. As the result, the echo data are acquired in a shorter time than by other beamformings; the error caused by the tissue motion during the data acquisition can be significantly decreased. Moreover, by using the prescribed displacement measurement methods after implementing the prescribed processing on the acquired echo data, the displacement vector or lateral one-direction displacement can be measured with a considerably high accuracy. A synthetic aperture may also be performed. An axial one-directional displacement measurement may also be performed.

Moreover, by using the strain tensor distribution data calculated from the displacement vector distribution data measured in this conduct form, a shear modulus distribution can be calculated (for instance, see ref. 12: C. Sumi, "Increasing accuracy of tissue shear modulus reconstruction using ultrasonic strain tensor measurement—Regularization and lateral modulation", in Acoustical Imaging, vol. 29, pp. 59-69, Springer, 2008). When measuring the shear modulus distribution, the material of a known shear modulus may set in the ROI as a reference. The reference region to be realized is a region of a shear modulus absolutely or relatively known or estimated in advance in the reference material or in the object. In order to measure the shear modulus distribution stably, the reference region should extend in the direction widely crossing the direction of the dominant tissue deformation. Then, for instance, when compressing the object using the transducer as a compressor, such a reference material is put between the transducer and the object. The reference may be assembled into the transducer itself.

The purpose of the measurements of the displacement vector distribution, strain tensor distribution and shear modulus distribution is to allow non-destructive and quantitative examinations or property evaluations of various objects, structures, substances, materials, living tissues etc. For instance, when dealing with human living tissues, the compression or vibration applied externally yields the change of such mechanical quantities and elasticity of tissues according to the lesion progress or change of tissue characteristics. The tissue displacement or deformation can also be dealt with by a spontaneous tissue motion such as a body motion, a respiratory, a heart motion, a pulsation etc. The shear modulus value or the geometrical distribution evaluated can be used for the differentiation of tissues (i.e., tissue characterization). Then, the display unit such as CRT described in paragraph 0111 can also exhibits such measured distributions as well as such values evaluated.

The methods and apparatuses can also be used for the monitoring of a treatment effectiveness or a temperature change generated by the radiotherapy such as a high intensity focus ultrasound, a leaser, an electromagnetic radio frequency wave or a microwave etc (see ref. 13: C. Sumi and H. Yanagimura, "Spatial inhomogeneity of tissue thermal parameter of Ebbini's model and its dependency on temperature," Jpn J Appl Phys, vol. 46, no. 7b, pp. 4790-4792, 2007). In this case, The display unit such as CRT described in paragraph 0111 can display the shear modulus calculated for the controlling the treatment before, during and after the treatment. Also the measured displacement vector distribution, displacement vector component distributions, strain tensor distribution, strain tensor component distributions, gradient distributions of strain tensor components, distribution of the temporal change etc can be display as a static or dynamic image together with the value at an arbitrary position or the temporal change as in a graph.

By using the display function of the ultrasound image, the spatial distributions of a bulk modulus or a density measured in a real-time can also be displayed. As the measurement results, the displacement vector distribution, displacement vector component distributions, strain tensor distribution, strain tensor component distributions, gradient distributions of the strain tensor components, distributions of the temporal change can also be displayed as a static or dynamic image. For the display of the displacement vector distribution measured, the vector line map can also be used. In addition, when measuring the temperature distribution, the thermal properties can also be calculated for the planning of the treatment (see ref. 13).

The methods and apparatuses can also be used for the monitoring of the treatment effectiveness (including the temperature change), and the controlling and planning for the interstitial type radiotherapies such as a high intensity focus ultrasound, a leaser, an electromagnetic radio frequency wave or a microwave etc. In addition, the methods and apparatuses can also be used for the monitoring of the effectiveness including the temperature change, and the controlling and planning of the treatment by an anti-cancer drug.

For the monitoring of the treatment effectiveness, if a mechanical source cannot be used, the degeneration, dilation, shrink and temperature change etc can also be detected by measuring the displacements or strains.

In addition, the methods and apparatuses can also be used for the non-destructive examinations for living tissues, objects, substances, materials at the growth or the producing by measuring or monitoring the displacement vector distribution, strain tensor distribution and shear modulus distribution.

Thus, the present invention supplies new methods and apparatuses (techniques) on the basis of the scanning using the steering beam with a single steering angle. As the result, the echo data are acquired in a shorter time than by other beamformings; the error caused by the tissue motion during the data acquisition can be significantly decreased. Moreover, by using the prescribed displacement measurement methods after implementing the prescribed processing on the acquired echo data, the displacement vector or lateral one-direction displacement can be measured with a considerably high accuracy. A synthetic aperture may also be performed. An axial one-directional displacement measurement may also be performed. The present invention also supplies a remarkable feature that allows the selection of the proper beamforming (e.g., conventional beamformings, lateral modulation, beam steering with a single steering angle and others), the proper displacement measurement method or the proper combination. That is, the function and/or method (i.e., a manual or automatic selection) is equipped for selecting them properly for every organ or tissue. That is, for every organ and tissue, the best echo imaging and the best displacement measurement are supplied. A frequency division method may also be used. When performing a synthetic aperture for the lateral modulation to be equipped together, the problems such as the low echo SNR caused due to a small ultrasound intensity transmission from an ultrasound element, a small VOF to be obtained can be mitigated using the virtual sources or receivers of the present invention.

The invention claimed is:

1. A displacement measurement apparatus comprising:
    at least one ultrasound sensor configured to transmit ultrasounds to an object in accordance with at least one drive signal, and detect ultrasound echo signals generated in the object to output echo signals;
    a driving and processing unit configured to supply the at least one drive signal to the sensor, and process the echo signals outputted from the sensor to obtain ultrasound echo data;
    a controller configured to control at least said driving and processing unit to yield an ultrasound echo data frame at each of plural different temporal phases based on the ultrasound echo data obtained by scanning the object using at least one ultrasound beam steered electrically and/or mechanically with at least one of (i) a single constant steering angle of 0°, (ii) a single constant non-zero steering angle, and (iii) a variable steering angle, the steering angle being with respect to a direction substantially orthogonal to a surface of the object, over a three-dimensional or two-dimensional orthogonal coordinate system involving orthogonal axes in at least two of axial, lateral, and elevational directions, said ultrasound echo data frame representing a plurality of the ultrasound echo data at plural positions, said ultrasound echo data having at least one of axial, lateral, and elevational carrier frequencies and a phase generated by at least one of axial, lateral, and elevational modulations yielded based on the at least one ultrasound beam, and said ultrasound echo data having one of local single octant spectra, local single quadrant spectra, and local single half-band-sided spectra in a frequency domain;
    a data processing unit configured to calculate a displacement at each position or distribution thereof in at least one of the axial, lateral, and elevational directions by implementing a predetermined displacement measurement method on the ultrasound echo data yielded at the plural different temporal phases with respect to the at least one of axial, lateral, and elevational carrier frequencies and the phase, or the one of the local single octant spectra, the local single quadrant spectra, and the local single half-band-sided spectra; and
    a display configured to display an image including the displacement or the distribution thereof.

2. The displacement measurement apparatus according to claim 1, wherein said controller is configured to set the orthogonal axes to make one of the axial, lateral, and elevational directions correspond to a direction of a dominant displacement of the object.

3. The displacement measurement apparatus according to claim 2, wherein in a case where said controller sets the orthogonal axes to make the lateral or elevational direction correspond to the direction of the dominant displacement of the object, said data processing unit calculates the displacement or the distribution thereof in the lateral or elevational direction.

4. The displacement measurement apparatus according to claim 1, wherein said data processing unit is configured to coarsely calculate a displacement vector or distribution thereof by implementing a predetermined multidirectional block matching algorithm on the ultrasound echo data frames yielded at the plural different temporal phases, and then finely calculate the displacement as a component of the displacement vector or the distribution thereof.

5. The displacement measurement apparatus according to claim 1, wherein said controller is configured to change the steering angle electrically and/or mechanically to control at least one of axial, lateral, and elevational modulation frequencies so as to increase a measurement accuracy of the displacement.

6. The displacement measurement apparatus according to claim 5, wherein said controller is configured to increase the steering angle electrically and/or mechanically to increase a carrier frequency of a direction orthogonal to the axial direction so as to increase a measurement accuracy of the displacement.

7. The displacement measurement apparatus according to claim 1, wherein said controller is configured to steer the at least one ultrasound beam electrically and/or mechanically to make a direction of the steered beam correspond to a direction of a dominant displacement so as to increase a measurement accuracy of the displacement.

8. The displacement measurement apparatus according to claim 1, wherein said controller is configured to rotate the coordinate system of the ultrasound echo data frame at or after beamforming to control at least one of the axial, lateral, and elevational carrier frequencies.

9. The displacement measurement apparatus according to claim 1, wherein said controller is configured to rotate the coordinate system of the ultrasound echo data frame at or after beamforming to obtain a high carrier frequency in at least one direction orthogonal to the axial direction.

10. The displacement measurement apparatus according to claim 1, wherein said controller is configured to sense, in a case of performing the mechanical beam steering, a mechanical steering angle which is used for reforming the coordinate system by rotation of the coordinate system at or after beamforming to make one of the axial, lateral, and elevational directions correspond to a direction of a dominant displacement.

11. The displacement measurement apparatus according to claim 1, wherein said data processing unit is configured to calculate a one-directional displacement or distribution thereof from mirrored set ultrasound echo data frames by using the predetermined displacement measurement method.

12. The displacement measurement apparatus according to claim 1, wherein said data processing unit is configured to calculate, in a case where the object moves dominantly in a direction, a one-directional displacement in the direction by dividing a difference of an instantaneous phase of echo data yielded at more than two phases with an instantaneous frequency in the direction.

13. The displacement measurement apparatus according to claim 1, wherein said data processing unit is configured to calculate, in a case where the object moves dominantly in a direction and no axis corresponds to the direction, a weighted summation of the displacements in the respective axes.

14. The displacement measurement apparatus according to claim 1, wherein said controller is configured to set at least one of virtual ultrasound sources and virtual ultrasound receivers behind or in front of a physical aperture regardless of at least one of geometry of the physical aperture and a focus position.

15. The displacement measurement apparatus according to claim 1, wherein:
said controller is configured to control at least said driving and processing unit to generate a large beam steering angle such that a higher carrier frequency in a direction orthogonal to the axial direction can be obtained than a Nyquist frequency determined by Nyquist theorem; and
said data processing unit is configured to widen a bandwidth of the direction orthogonal to the axial direction by padding zeros in frequencies higher than the Nyquist frequency, or interpolate a beam pitch in a spatial domain.

16. The displacement measurement apparatus according to claim 1, wherein said data processing unit is configured to remove at least one of side lobes and grating lobes, or separate at least one of crossed ultrasound beams, waves, and plural signals arrived from arbitrary directions in a multidimensional frequency domain.

17. The displacement measurement apparatus according to claim 1, wherein said data processing unit is configured to use harmonic echo signals to derive simultaneous equations at each position for calculating one of a three-dimensional displacement vector, a two-dimensional displacement vector, and a displacement.

18. The displacement measurement apparatus according to claim 1, wherein said data processing unit is configured to calculate at least one of strain tensor components, a strain, strain rate tensor components, a strain rate component, acceleration vector components, an acceleration, velocity vector components, a velocity, corresponding distribution, and corresponding time series by implementing at least one of a spatial differential filter and a temporal differential filter with respect to at least one of a calculated displacement vector, a displacement, corresponding distribution, and corresponding time series.

19. The displacement measurement apparatus according to claim 1, wherein:
said data processing unit is configured to calculate at least one of displacement vector components or a displacement, strain tensor components, principle strains or a strain, strain rate tensor components, principle strain rates or a strain rate, acceleration vector components or an acceleration, velocity vector components or a velocity, corresponding distribution, and corresponding time series; and
said a display is configured to display at least one of the displacement vector components or the displacement, the strain tensor components, the principle strains or the strain, the strain rate tensor components, the principle strain rates or the strain rate, the acceleration vector components or the acceleration, the velocity vector components or the velocity, the corresponding distribution, the corresponding time series, an rf-echo image or a B-mode image obtained using at least one of divided spectra, windowed spectra and original spectra, and an rf-echo image or a B-mode image obtained using divided or windowed spectra of a superposition of at least one of divided spectra, windowed spectra and original spectra.

20. The displacement measurement apparatus according to claim 1, further comprising at least one sensor configured to sense one selected from the group consisting of a magnetic nuclear resonance signal, electromagnetic waves, and light.

* * * * *